(12) United States Patent
Pikov

(10) Patent No.: US 12,268,872 B2
(45) Date of Patent: Apr. 8, 2025

(54) DEVICES, SYSTEMS, AND METHODS FOR DELIVERING THERAPY TO INTESTINAL MUSCLE

(71) Applicant: EnteroMed Ltd, Tsim Sha Tsui (HK)

(72) Inventor: Victor Eugene Pikov, Pasadena, CA (US)

(73) Assignee: EnteroMed Ltd, Tsim Sha Tsui (HK)

( * ) Notice: Subject to any disclaimer, the term of this patent is extended or adjusted under 35 U.S.C. 154(b) by 697 days.

(21) Appl. No.: 17/466,933

(22) Filed: Sep. 3, 2021

(65) Prior Publication Data

US 2021/0393954 A1 Dec. 23, 2021

Related U.S. Application Data

(63) Continuation of application No. PCT/CN2020/077799, filed on Mar. 4, 2020.
(Continued)

(51) Int. Cl.
*A61N 1/36* (2006.01)
*A61N 1/08* (2006.01)
(Continued)

(52) U.S. Cl.
CPC .......... *A61N 1/36007* (2013.01); *A61N 1/08* (2013.01); *A61B 5/0245* (2013.01); *A61B 5/392* (2021.01); *A61N 1/0509* (2013.01)

(58) Field of Classification Search
CPC .... A61N 1/36007; A61N 1/08; A61B 5/0245; A61B 5/392
See application file for complete search history.

(56) References Cited

U.S. PATENT DOCUMENTS

| 6,091,992 A | 7/2000 | Bourgeois et al. |
| 6,243,607 B1 | 6/2001 | Mintchev et al. |

(Continued)

FOREIGN PATENT DOCUMENTS

| CN | 101060884 A | 10/2007 |
| CN | 105498085 A | 4/2016 |

(Continued)

OTHER PUBLICATIONS

Cheng, J. et al. (2020). "Potential of electrical neuromodulation for inflammatory bowel disease," Inflamm Bowel Dis. 26:1119-1130.
(Continued)

*Primary Examiner* — Joseph M Dietrich
(74) *Attorney, Agent, or Firm* — Cooley LLP

(57) ABSTRACT

Systems for delivering therapy to an intestinal muscle in a patient may comprise a cardiac sensor, an intestinal sensor, an implantable pulse generator and a signal delivery device. The signal delivery device may be configured to deliver a stimulation signal to the muscle. The implantable pulse generator may comprise a microcontroller configured to receive cardiac data from the cardiac sensor and calculate a heart rate parameter therefrom, receive intestinal activity data from the intestinal sensor and calculate an intestinal activity parameter therefrom, determine a physiological state of a patient based on the parameters, adjust a stimulation parameter of the stimulation signal based on the determined state, and instruct the signal delivery device to deliver an adjusted stimulation signal.

27 Claims, 10 Drawing Sheets

Related U.S. Application Data

(60) Provisional application No. 62/814,649, filed on Mar. 6, 2019.

(51) Int. Cl.
*A61B 5/0245* (2006.01)
*A61B 5/392* (2021.01)
*A61N 1/05* (2006.01)

(56) References Cited

U.S. PATENT DOCUMENTS

| | | |
|---|---|---|
| 6,449,511 B1 | 9/2002 | Mintchev et al. |
| 6,735,474 B1 | 5/2004 | Loeb et al. |
| 6,826,428 B1 | 11/2004 | Chen et al. |
| 6,853,862 B1 | 2/2005 | Marchal |
| 7,664,551 B2 | 2/2010 | Cigaina |
| 7,778,711 B2 | 8/2010 | Ben-David et al. |
| 7,925,351 B2 | 4/2011 | Khawaled et al. |
| 8,095,218 B2 | 1/2012 | Gross et al. |
| 8,285,373 B2 | 10/2012 | Ternes et al. |
| 8,355,797 B2 | 1/2013 | Caparso et al. |
| 8,406,877 B2 | 3/2013 | Smith et al. |
| 8,594,811 B2 | 11/2013 | Chen et al. |
| 8,600,521 B2 | 12/2013 | Armstrong et al. |
| 8,666,495 B2 | 3/2014 | Harel et al. |
| 10,922,133 B2 | 2/2021 | He et al. |
| 12,017,073 B2 | 6/2024 | Pikov et al. |
| 2003/0055463 A1 | 3/2003 | Gordon et al. |
| 2005/0015117 A1 | 1/2005 | Gerber |
| 2005/0055063 A1 | 3/2005 | Loeb et al. |
| 2005/0060005 A1 | 3/2005 | Boggs, II et al. |
| 2005/0143783 A1 | 6/2005 | Boveja et al. |
| 2005/0209653 A1 | 9/2005 | Herbert et al. |
| 2006/0235477 A1 | 10/2006 | Rom |
| 2007/0016262 A1 | 1/2007 | Gross et al. |
| 2007/0027492 A1 | 2/2007 | Maschino et al. |
| 2007/0093870 A1 | 4/2007 | Maschino |
| 2009/0036945 A1 | 2/2009 | Chancellor et al. |
| 2009/0062881 A1* | 3/2009 | Gross ............ A61N 1/36007 607/40 |
| 2009/0138061 A1 | 5/2009 | Stephens et al. |
| 2009/0240194 A1 | 9/2009 | Keimel et al. |
| 2010/0211135 A1 | 8/2010 | Caparso et al. |
| 2011/0295335 A1* | 12/2011 | Sharma ............ A61N 1/36139 607/40 |
| 2012/0130444 A1 | 5/2012 | Wei et al. |
| 2012/0197338 A1 | 8/2012 | Su et al. |
| 2012/0259382 A1 | 10/2012 | Trier et al. |
| 2012/0316451 A1 | 12/2012 | Province et al. |
| 2013/0150940 A1 | 6/2013 | Wilson et al. |
| 2013/0158618 A1 | 6/2013 | Libbus et al. |
| 2013/0238047 A1 | 9/2013 | Libbus et al. |
| 2013/0241745 A1 | 9/2013 | Colvin, Jr. et al. |
| 2013/0289647 A1 | 10/2013 | Bhadra et al. |
| 2014/0046398 A1 | 2/2014 | Sachs et al. |
| 2014/0249595 A1 | 9/2014 | Chancellor et al. |
| 2014/0253038 A1 | 9/2014 | Posa |
| 2014/0277250 A1 | 9/2014 | Su et al. |
| 2015/0134027 A1 | 5/2015 | Kaula et al. |
| 2015/0142082 A1 | 5/2015 | Simon et al. |
| 2015/0196351 A1 | 7/2015 | Stone et al. |
| 2016/0303376 A1 | 10/2016 | Dinsmoor et al. |
| 2016/0367814 A1 | 12/2016 | Pless et al. |
| 2017/0120055 A1 | 5/2017 | Rezal et al. |
| 2017/0143972 A1 | 5/2017 | Hershey et al. |
| 2017/0203103 A1 | 7/2017 | Levine et al. |
| 2017/0203110 A1 | 7/2017 | Imran |
| 2018/0193643 A1 | 7/2018 | Chen et al. |
| 2019/0060647 A1 | 2/2019 | Su et al. |
| 2020/0188671 A1 | 6/2020 | Lovett |
| 2020/0360696 A1 | 11/2020 | Pikov et al. |

FOREIGN PATENT DOCUMENTS

| | | |
|---|---|---|
| CN | 105521561 A | 4/2016 |
| CN | 106345056 A | 1/2017 |
| CN | 107789733 A | 3/2018 |
| CN | 107921263 A | 4/2018 |
| CN | 108463163 A | 8/2018 |
| CN | 207734348 U | 8/2018 |
| GB | 1 577 682 A | 10/1980 |
| JP | 2002-102360 A | 4/2002 |
| JP | 2006-508768 A | 3/2006 |
| WO | WO-2004/000416 A1 | 12/2003 |
| WO | WO-2006/010025 A2 | 1/2006 |
| WO | WO-2006/010025 A3 | 1/2006 |
| WO | WO-2010/067360 A2 | 6/2010 |
| WO | WO-2010/067360 A3 | 6/2010 |
| WO | WO-2016/137926 A1 | 9/2016 |
| WO | WO-2017/002104 A1 | 1/2017 |
| WO | WO-2018/053336 A1 | 3/2018 |
| WO | WO-2018/152064 A1 | 8/2018 |

OTHER PUBLICATIONS

De las Casas, S.G et al. (2019). "Sacral nerve stimulation for constipation: long-term outcomes," Techniques in coloproctology 23:559-564.

Guo, J. et al. (2019). "Sacral nerve stimulation improves colonic inflammation mediated by autonomic-inflammatory cytokine mechanism in rats," Neurogastroenterol Motil. 31:e13676.

Huang, Z. et al. (2019). "Sacral nerve stimulation with appropriate parameters improves constipation in rats by enhancing colon motility mediated via the autonomic-cholinergic mechanisms," Am J Physiol Gastrointest Liver Physiol. 317:G609-G617.

International Search Report mailed on May 29, 2020, for PCT Application No. PCT/CN2020/077799, filed on Mar. 4, 2020, 5 pages.

International Search Report mailed on Aug. 18, 2020, for PCT Application No. PCT/CN2020/090615, filed on May 15, 2020, 3 pages.

Jin, H. et al. (2017). "Anti-inflammatory effects and mechanisms of vagal nerve stimulation combined with electroacupuncture in a rodent model of TNBS-induced colitis," Am J Physiol Gastrointest Liver Physiol. 313:G192-G202.

Li, S. et al. (2017). "Pulse Width-Dependent Effects of Intestinal Electrical Stimulation for Obesity: Role of Gastrointestinal Motility and Hormones," Obes. Surg. 27:70-77.

Liu, J. et al. (2011). "Hypoglycemic Effects of Intraluminal Intestinal Electrical Stimulation in Healthy Volunteers," Obes. Surg. 21:224-230.

Ni, M. et al. (2019). "Anti-Inflammatory Effects and Mechanisms of Sacral Nerve Stimulation Performed Via Acupuncture Needles on Ulcerative Colitis," Gastroenterology 156:S-585.

Pasricha, T.S. et al. (2020). "Sacral nerve stimulation prompts vagally-mediated amelioration of rodent colitis," Physiol Rep. 8:e14294, 7 total pages.

Tu, L. et al. (2020). "Anti-inflammatory effects of sacral nerve stimulation: a novel spinal afferent and vagal efferent pathway," Am J Physiol Gastroint Liver Physiol. 318:G624-G634.

Tu, L. (2020). "Sacral nerve stimulation ameliorates colonic barrier functions in a rodent model of colitis," Neurogastroenterology & Motility, p. e13916, 49 total pages.

Written Opinion of the International Searching Authority mailed on May 29, 2020, for PCT Application No. PCT/CN2020/077799, filed on Mar. 4, 2020, 5 pages.

Written Opinion of the International Searching Authority mailed on Aug. 18, 2020, for PCT Application No. PCT/CN2020/090615, filed on May 15, 2020, 4 pages.

Yin, J. et al. (2007). "Potential of Intestinal Electrical Stimulation for Obesity: A Preliminary Canine Study," Obesity 15:1133-1138.

Zhang, N. et al. (2020). "A novel method of sacral nerve stimulation for colonic inflammation," Neurogastroenterol Motil., p. e13825, 13 total pages.

(56) References Cited

OTHER PUBLICATIONS

Corrected Notice of Allowability mailed on May 20, 2024, for U.S. Appl. No. 16/874,522, filed May 14, 2020, 11 pages.
Non-Final Office Action mailed on Aug. 23, 2023, for U.S. Appl. No. 16/874,522, filed May 14, 2020, 18 pages.
Notice of Allowance mailed on Feb. 15, 2024, for U.S. Appl. No. 16/874,522, filed May 14, 2020, 13 pages.

* cited by examiner

DEVICES, SYSTEMS, AND METHODS FOR DELIVERING THERAPY TO INTESTINAL MUSCLE

CROSS-REFERENCE TO RELATED APPLICATIONS

This application is a continuation of International Application No. PCT/CN2020/077799, filed on Mar. 4, 2020, which claims priority to U.S. Provisional Application Ser. No. 62/814,649, filed on Mar. 6, 2019, the content of each of which is hereby incorporated by reference in its entirety.

TECHNICAL FIELD

This invention relates generally to the field of tissue stimulation, and more particularly, to new and useful devices, systems, and methods for non-surgical screening of patients, delivering electrical stimulation, and/or adjusting delivery of electrical stimulation using autonomic nervous system parameters and intestinal activity parameters.

BACKGROUND

The increase in prevalence of intestinal disorders (such as pseudo-obstruction, functional dyspepsia, gastroparesis, esophageal dysmotility, intestinal dysmotility, colonic inertia, pancreatitis, ulcerative colitis, Crohn's disease, chronic constipation, chronic fecal incontinence, functional abdominal pain, irritable bowel syndrome) and metabolic disorders (such as type 2 diabetes mellitus, obesity, dyslipidemia, cardiometabolic disease, non-alcoholic fatty liver disease, chronic kidney disease, polycystic ovary syndrome, hypertension) constitutes a severe unmet medical need.

Conventional treatment of these disorders can include delivery of electrical stimulation to a particular anatomical location, for example, intestinal tissue. The stimulation may be delivered using implantable systems that include an implantable pulse generator and one or more leads. A clinician may need to set and later adjust a variety of stimulation parameters or programs for the patient. Generally, there are several stimulation parameters that are initially set up by the clinician with the patient's feedback. The initial setup typically occurs soon after the implantation. The clinician or patient then uses an external programmer to change between these programs when the patient's state and/or stimulation comfort level has changed. However, in many cases, the preset stimulation levels established at implantation may become unsuitable for the patient over time due to changes in lead placement, scar tissue build-up around the lead, or due to changes in therapy efficacy or disease progression. These changes may require the clinician or patient to periodically adjust the stimulation settings, which typically requires office visits by the patient. Accordingly, there is a need for improved devices and techniques for delivering stimulation to a patient, customizing a patient's stimulation parameters, and/or automatically setting and adjusting stimulation levels.

Additionally, many patients have a stimulation delivery device implanted without an initial pre-screening to inform the patient and/or care provider about the likely efficacy of the treatment. In some instances, patients have a stimulation delivery device implanted, but do not receive sufficient therapy efficacy to justify the cost and risks associated with the implantation surgery. Accordingly, there is a need for improved devices, systems, and techniques for non-surgical screening of patients to evaluate stimulation therapy efficacy before exposing patients to the costs and risks associated with device implantation surgery.

BRIEF SUMMARY

Described here are systems and methods for delivering therapy, for example, stimulation, to tissue (e.g., intestinal muscle), and mechanisms for controlling these systems.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION

Figure 1:
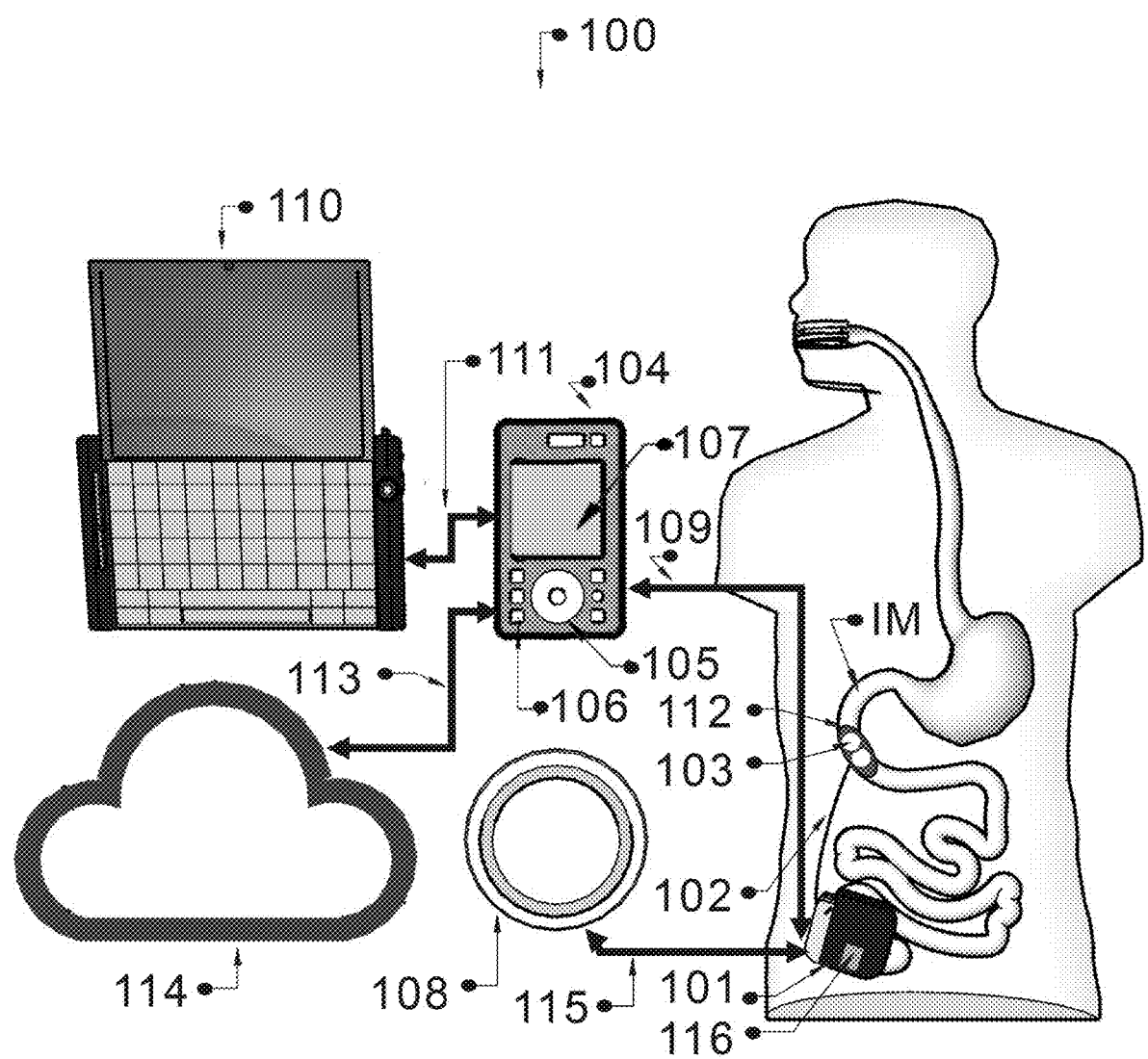
FIG. 1 is a schematic diagram of an illustrative system for providing non-surgical screening and therapy to a patient.

Described here are devices, systems, and methods for treating one or more intestinal (such as pseudo-obstruction, functional dyspepsia, gastroparesis, esophageal dysmotility, intestinal dysmotility, colonic inertia, pancreatitis, ulcerative colitis, Crohn's disease, chronic constipation, chronic fecal incontinence, functional abdominal pain, irritable bowel syndrome) or metabolic disorders (such as type 2 diabetes mellitus, obesity, dyslipidemia, cardiometabolic disease, non-alcoholic fatty liver disease, chronic kidney disease, polycystic ovary syndrome, hypertension) by providing electrical stimulation therapy to a target tissue, for example, muscular tissue in a portion of the small intestine. The devices, systems, and methods may generally provide for controllably stimulating the target tissue. For example, the devices, systems, and methods may adjust one or more stimulation parameters of a stimulation signal using data collected with one or more sensors. The devices, system and methods may calculate one or more physiological parameters and may determine one or more physiological states. The devices, systems, and methods described here may facilitate intestinal motility in order to, for example, improve intestinal food transit, reduce the sympathetic tone, increase insulin sensitivity, increase glucose tolerance, decrease plasma glucose concentration, reduce subcutaneous fat content, increase secretion of glucagon-like-peptide-1 (GLP-1), reduce plasma glycated hemoglobin (HbA1c) concentration, reduce plasma triglyceride concentration in at least one chronic intestinal or metabolic disorder: pseudo-obstruction, functional dyspepsia, gastroparesis, esophageal dysmotility, intestinal dysmotility, colonic inertia, pancreatitis, ulcerative colitis, Crohn's disease, chronic constipation, chronic fecal incontinence, functional abdominal pain, irritable bowel syndrome, type 2 diabetes mellitus, obesity, dyslipidemia, cardiometabolic disease, non-alcoholic fatty liver disease, chronic kidney disease, polycystic ovary syndrome, hypertension, or a combination of any of the above.

As used herein, the terms "stimulating" and "stimulation" refer generally to signals applied to a patient to elicit a muscular response (e.g., electrical stimulus). Unless otherwise specified, the signals may have an activating or excitatory effect on the target muscle. As used herein, the term "stimulator" applies generally to a device that generates and/or directs stimulation signals. Although described herein as stimulating intestinal muscle of a patient, the stimulators described here may also be used to stimulate other tissues.

As used herein, the term "physiological parameter" refers generally to a measurable metric extracted from data collected using a sensor. For example, measurable autonomic nervous system parameters (i.e., heart rate parameters) may be extracted from cardiac data (e.g., electrocardiographic data) and measurable intestinal activity parameters may be extracted from intestinal sensor data (e.g., myoelectrical intestinal activity data, intestinal temperature data). Physiological parameters may be extracted using a variety of time-domain calculation methods and frequency-domain calculation methods. For example, with respect to the cardiac data, the time-domain calculation may be used to measure the heart rate variability (HRV) in the beat-to-beat fluctuations in the rhythm of the heart from electrocardiographic data. The frequency-domain calculation may then be applied to the HRV data to calculate the power of the low frequency (LF) band, the power of the high frequency (HF) band, and the LF/HF power ratio. The power of the LF band (0.04 Hz to 0.15 Hz) measures the sympathetic influence on the heart, while the power of the HF band (0.15 Hz to 0.40 Hz) measures the parasympathetic influence on the heart. The LF/HF power ratio indicates the functional prevalence of the sympathetic activity over the parasympathetic activity. Thus, the heart rate parameters may include a time-domain parameter (e.g., average heart rate, heart rate variability) and/or a frequency-domain parameter (e.g., power of the LF band, power of the HF band, LF/HF power ratio). With respect to the intestinal activity data, the frequency-domain calculation may be used to determine intestinal slow wave activity (ISW) parameters, (e.g. ISW frequency and ISW power) from the low-frequency band of intestinal myoelectrical data and intestinal bursting (IB) activity parameters (e.g. IB duration, IB spike number, and IB spike frequency) from the high-frequency band of intestinal myoelectrical data. Intestinal activity data may also include intestinal temperature data. Thus, the intestinal activity parameters may include ISW parameters (e.g., ISW frequency and ISW power), IB activity parameters (e.g., IB duration, IB spike number, IB spike frequency), and/or intestinal temperature (e.g., averaged intestinal temperature over time (e.g., about 1 minute, about 10 minutes, about 1 hour, from about 1 minute to about 1 hour and/or any values or subranges therein)).

As used herein, the term "physiological state" refers generally to a category assigned to a particular level of activity of one or more internal organs or systems in the patient's body. For example, the physiological state of "food consumption" refers to activation of gastrointestinal activity following consumption of some type of food (e.g. liquid, light meal, or heavy meal). This can be contrasted to the physiological state of "fasting", characterized by a by idle gastrointestinal activity.

As used herein, the term "stimulation parameter" refers generally to a setting of the electrical stimulation therapy applied to a tissue (e.g., intestinal muscle) using a signal delivery device (e.g., an implantable signal delivery device and/or a temporary signal delivery device). For example, stimulation parameters may include a stimulation amplitude, a pulse width, a frequency, a burst interval, an elapsed duration, and/or other suitable settings of the electrical stimulation therapy. As used herein, the term "stimulation signal" refers to the output of the stimulator that is generated based on the combination of stimulation parameters.

In some variations of the devices, systems, and methods described herein, the amplitude of the pulses may be between about 0.1 mA and about 30 mA, the pulse width may be between about 20 microseconds and about 100 milliseconds, including all values and subranges therein (e.g., about 4 milliseconds, from about 1 millisecond to about 5 milliseconds, from about 1 millisecond to about 10 milliseconds), and/or the frequency of the pulses may be between about 0.01 Hz and about 50 Hz, including all values and subranges therein (e.g., about 0.2 Hz, from about 0.01 Hz to about 1 Hz, from about 0.01 Hz to about 5 Hz). In some embodiments, the stimulation signal may comprise rectangular pulses and/or complex electrical pulses. In variations in using complex electrical pulses, the complex electrical pulses may comprise multi-level pulses, biphasic pulses, non-rectangular pulses, pulses with varying inter-pulse intervals, pulses with varying amplitude, or a combination thereof. The system may deliver the pulses constantly or may intermittently deliver a series of pulses. For example, in some variations, the system may deliver a train of pulses during signal-ON times, and the train of pulses may be separated by signal-OFF times when pulses are not delivered. The intermittently-delivered stimulation signal may have a duty cycle represented as a signal-ON time portion of a stimulation period. In some variations, the duty cycle may be between about 0.1% and about 50%, including all values and sub-ranges therebetween (e.g., about 10% with 10 sec ON and 90 sec OFF, less than about 10%, from about 0.1% to about 5%, from about 0.1% to about 10%).

Systems

The intestinal muscle stimulation systems described here may generally comprise a sensor (e.g., wearable and/or implantable), an intestinal muscle stimulation device (e.g., an implantable pulse generator), one or more signal delivery devices (implantable and/or temporary), and an external programmer. In some variations, the systems may further comprise a computer, a power charger for the intestinal muscle stimulation device, and/or a server. FIG. 1 schematically illustrates an embodiment of an intestinal muscle stimulation system 100. As shown there, the stimulation system 100 may comprise an implantable pulse generator 101, a signal delivery device 112, an external programmer 104, a charging antenna 108, a computer 110, and a server 114. The intestinal muscle stimulation system 100 is shown in FIG. 1 positioned relative to the general anatomy of the intestinal muscle (labeled "IM" in FIG. 1) of a patient. In particular, the signal delivery device 112 is depicted implanted within an intestinal wall of a patient, and the pulse generator 101 is depicted implanted in a subcutaneous pocket in the abdomen.

The systems described here may generally comprise one or more sensors (e.g., wearable and/or implantable). The sensors may be coupled to (e.g., inside or coupled to the outside) the implantable pulse generator, or may be separate from the implantable pulse generator. In some variations, one or more of the sensors may be configured to measure data from which an autonomic nervous system parameter may be extracted (e.g., the sensors may be cardiac (e.g., electrocardiographic) sensors) or from which an intestinal activity parameter may be extracted (e.g., the sensors may be intestinal activity sensors, such as, intramuscular myoelectrical sensors or temperature sensors such as intestinal thermal probes). In some instances, it may be beneficial to utilize both an autonomic nervous system sensor (a cardiac sensor) and an intestinal activity sensor to inform adjustment of one or more of the stimulation parameters, as use of both data sets may allow for a more accurate determination of a physiological state (especially in distinguishing physiological states related to, versus unrelated to, food consumption) of a patient, which may result in a reduction of unwanted side effects and an improvement of therapy efficacy. In some embodiments, a plurality of autonomic nervous system sensors (e.g., two, three, four or more) and/or a plurality of intestinal activity sensors (e.g., two, three, four, or more) may be used. For example, the system may comprise an autonomic nervous system sensor (e.g., a cardiac sensor), a first intestinal activity sensor such as an intestinal myoelectical electrode, and a second intestinal activity sensor such as an intestinal thermal probe. The cardiac sensor may be placed near the heart, while the intestinal sensor (e.g., intestinal myoelectrical electrode and/or the intestinal thermal probe) may be placed in the intestinal muscle.

In some variations, additional or other sensors may be used to assist in calculating physiological parameters, for example, when patient has other diseases or health conditions. For example, in a variation in which the patient has a restless leg syndrome, the intestinal myoelectrical sensor may mistakenly detect leg movement as intestinal movement. In this circumstance, it may be beneficial to include a myoelectrical sensor positioned on a leg of the patient to assist in distinguishing intestinal activity versus leg activity.

Implantable Pulse Generator

As mentioned above, the systems described here may comprise an intestinal muscle stimulation device, for example, an implantable pulse generator. The implantable pulse generator 101 may be configured to generate and transmit stimulation signals to the signal delivery device 112. In certain embodiments, the implantable pulse generator 101 may comprise a microcontroller interconnected with non-transitory computer-readable memory containing the instructions for the microcontroller, and further connected with input/output devices (e.g., wired or wireless transceivers), power management circuitry, and/or other suitable electrical components (not shown in FIG. 1), as described in more detail below with reference to FIG. 2. The computer-readable memory may comprise volatile and/or nonvolatile memory, e.g., read-only memory (ROM), random access memory (RAM), magnetic memory, flash memory, and/or others. In some embodiments, the implantable pulse generator 101 may also comprise specific hardware components having hard-wired logic (e.g., field-programmable gate arrays) for performing the operations, methods, or processes or with any combination of programmed data processing components and specific hardware components. In some variations, the implantable pulse generator 101 may transmit stimulation signals to the signal delivery device 112 using a UHF and/or a VHF band.

In a particular embodiment, the implantable pulse generator 101 may comprise a sensor 116 in electrical communication with the microcontroller of the implantable pulse generator 101. In other embodiments, the sensor 116 may be positioned remotely from the implantable pulse generator 101 and may be coupled to the implantable pulse generator 101 with a suitable link (e.g., a wired or wireless link). In certain embodiments, the sensor 116 may be connected to the implantable pulse generator 101 with a lead 102 and positioned within the lead electrode 103. The system 100 may comprise a single sensor 116, or multiple sensors 116 depending on factors including patient condition, patient diagnosis, and/or clinician preference. In some variations, the sensor 116 may be an autonomic nervous system sensor (a cardiac sensor) and/or an intestinal activity sensor. In some variations, the sensor 116 may comprise at least one of an electrocardiographic activity sensor, a myoelectrical activity sensor, a temperature sensor (e.g., an intestinal thermal probe), and/or a heart rate monitor. In variations utilizing an intestinal thermal probe as a temperature sensor, the intestinal thermal probe may be a resistance temperature detector (e.g., made from platinum), a thermocouple (e.g., made from platinum and rhodium), a thermistor (e.g., made from a semiconductor), and/or a PIN diode (e.g., made from p-type, i-type, and n-type amorphous silicon). In some variations, a single sensor may be used to measure both cardiac and intestinal activity. For example, in some of these variations, a single sensor may be used to measure both electrocardiographic activity and myoelectrical intestinal activity. In other variations, separate sensors may be used to measure cardiac and intestinal activity. For example, a cardiac sensor may be used to measure electrocardiographic activity and an intestinal sensor may be used to measure myoelectrical intestinal activity.

Figure 2:
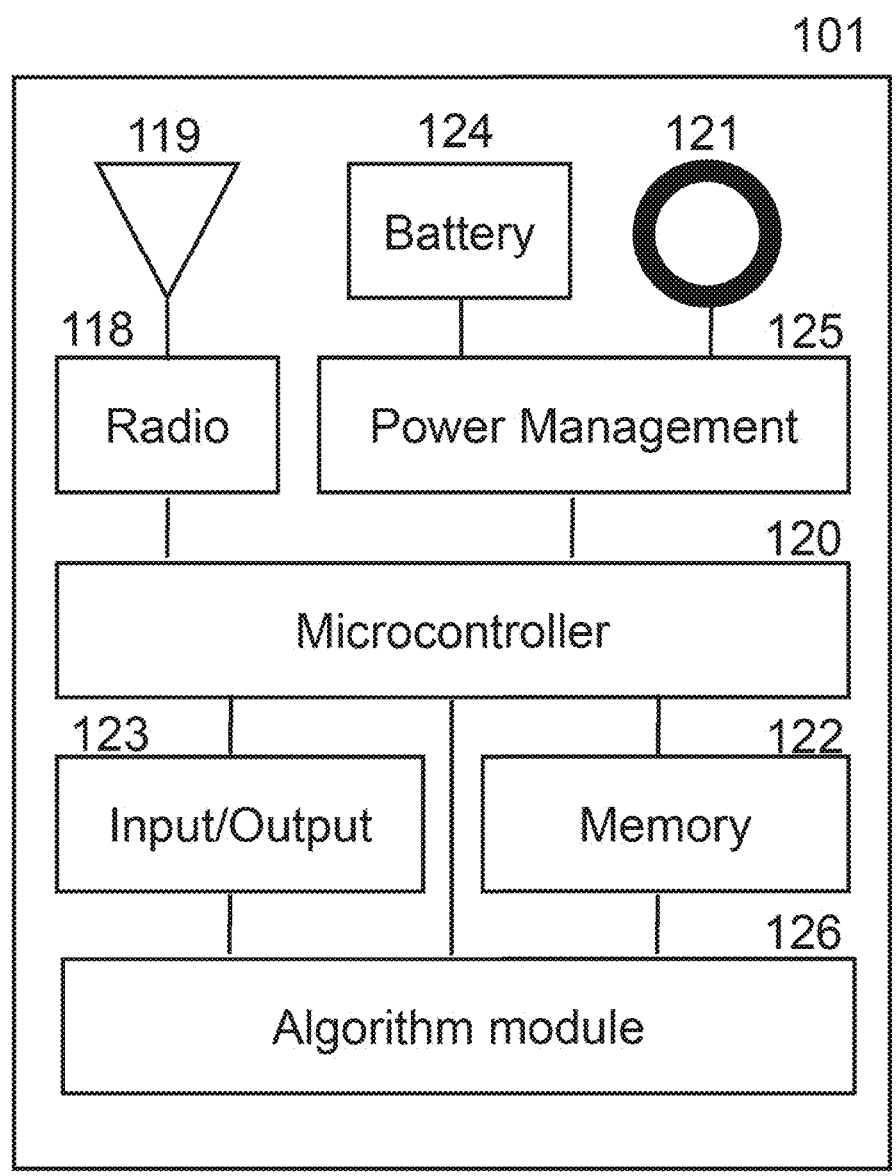
FIG. 2 is a block diagram depicting components of an exemplary implantable pulse generator.

FIG. 2 is a functional block diagram illustrating components of the implantable pulse generator 101 of FIG. 1. As shown in FIG. 2, the implantable pulse generator 101 may comprise a radio 118, a radio antenna 119, a microcontroller 120, a charging coil 121, a memory module 122, an input/output module 123, a battery 124, a power management circuit 125, and an algorithm module 126. The radio antenna 119 may create a bidirectional wireless data link 109 to communicate with the external programmer 104, and the charging coil 121 (e.g., an induction coil) may create a bidirectional wireless power communication link 115 with the wireless charging antenna 108 for recharging the battery 124 via the power management circuit 125. The microcontroller 120 may be coupled to the input/output module 123 and the memory module 122.

The implantable pulse generator 101 may generally be configured to receive data from the one or more sensors, calculate physiological parameters from the data received, determine a physiological state from the physiological parameters, adjust a stimulation parameter, and instruct the signal delivery device 112 to deliver a stimulation signal comprising the adjusted stimulation parameter. The pulse generator 101 may also be configured to establish correlation weights between physiological parameters and physiological states during a learning phase. The pulse generator 101 may be configured to subsequently automatically start stimulation, stop stimulation, and/or adjust one or more stimulation parameters based, at least in part, on the correlation weights between physiological parameters and physiological states learned during a learning phase of the algorithm in the algorithm module 126, as will be discussed in more detail herein, and the current physiological parameters and physiological state of the patient.

For example, in a variation in which the system comprises a cardiac sensor and an intestinal sensor, the implantable pulse generator 101 may be configured to receive cardiac data from the cardiac sensor and calculate a physiological parameter (e.g., a heart rate parameter) from the cardiac data, receive intestinal activity data from the intestinal sensor and calculate a physiological parameter (e.g., an intestinal activity parameter) from the intestinal activity data, determine a physiological state of the patient based on the physiological parameters (e.g., the heart rate parameter and the intestinal activity parameter), adjust a stimulation parameter based on the determined state, and instruct the signal delivery device 112 to deliver an adjusted stimulation signal comprising the adjusted intestinal muscle stimulation parameter.

While the therapy system 100 is described above with the algorithm module 126 residing in the implantable pulse generator 101, it need not. For example, in some variations, the external programmer 104, the computer 110, and/or the cloud server 114 may comprise the algorithm module 126, and the implantable pulse generator 101 may transfer current sensor data and/or calculated physiological parameters to the external programmer 104, the computer 110, and/or the cloud server 114 via the bidirectional wireless data link 109. In some variations, portions of the algorithm module 126 may be contained in the implantable pulse generator 101 and one or more of the external programmer 104, the computer 110, and the cloud server 114. In some variations, a database of sensor measurements, physiological parameters, physiological states, and/or correlation weights may be stored in the memory module 122 and may be uploaded to or downloaded from the external programmer 104, the computer 110, and the cloud server 114.

The power management circuit 125 may comprise a frequency modulator, an amplitude modulator, and/or other suitable circuitry for modulating inductive protocols. The microcontroller 120 may be configured to provide control signals to and receive data from the radio 118 and to communicate with the power management circuit 125. In certain embodiments, the microcontroller 120 may include a detector or a decoder with associated software and/or firmware to perform detection/decoding functions and process received signals. The memory module 122 may include volatile and/or nonvolatile storage. The memory module 122 may be configured to store data received from, as well as instructions for, the microcontroller 120. The input/output module 123 may include logic components that receive and interpret input from the external programmer 104 as well as logic components that output information to the external programmer 104 (FIG. 1). The microcontroller 120, the input/output module 123, and the memory module 122 may communicate with the algorithm module 126. The algorithm module 126 may contain a computer program, with its source code written in a conventional programming language (e.g., the C++ or C programming languages) and may be executed by the microcontroller 120.

Figure 3:
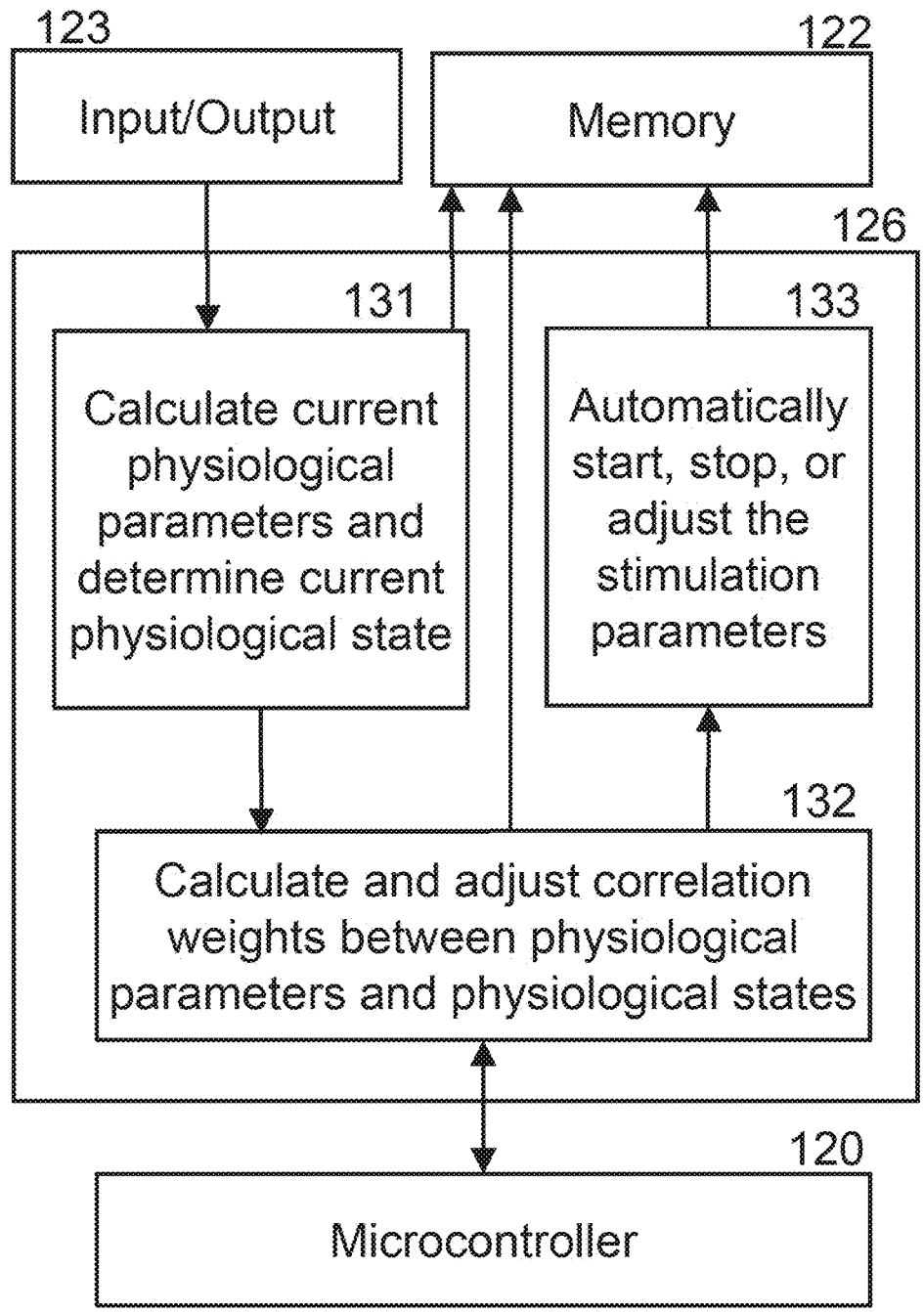
FIG. 3 is a block diagram depicting components and software modules of an exemplary implantable pulse generator.

FIG. 3 is a block diagram showing the algorithm module 126 of the implantable pulse generator 101 of FIG. 2. For the ongoing monitoring of the physiological parameters, the implantable pulse generator 101 (e.g., the algorithm module) may periodically receive the sensor data from the input/output module 123, calculate current physiological parameters, and determine a current physiological state 131. The implantable pulse generator 101 may use the current physiological parameters and physiological states 131 to calculate and adjust correlation weights between physiological parameters and physiological states 132. The current physiological parameters, physiological states, and correlation weights may be added to the database in the memory module 122. Any of a variety of suitable database organizations can be utilized, including a flat file system, hierarchical database, relational database, or distributed database. The microcontroller 120 may periodically execute the algorithm module on a continuous, ongoing basis (or as needed or requested) to recognize any trends in the collected information which may, in some instances, be used to automatically start, stop, or adjust the stimulation parameters 133. Current stimulation parameters may be added to the database in the memory module 122. As will be described in more detail herein, the algorithm may have two phases-a learning phase and an automatic operation phase. Generally, the algorithm may calculate or otherwise receive the physiological parameter data and correlate it with the patient-provided physiological states during the learning phase. In the automatic operation phase, the algorithm may calculate or otherwise receive the physiological parameter data and start, stop, or adjust the signal delivery based on correlation weights between the physiological parameters and physiological states, and the signal parameters assigned to specific physiological states established during the learning phase.

In the learning phase, the physiological state may be defined by and/or received from a patient, determined by the algorithm, or both, while in the automatic operation phase, the physiological state may be determined by the system (e.g., algorithm) alone, without patient input. Each physiological state may be associated with an initial stimulation program and/or initial stimulation signal parameters, which may be preset by a clinician, a device company representative, and/or other member of authorized personnel and may, in instances, later be adjusted by the patient. In some variations, the physiological states that may be associated with an initial stimulation program and/or initial stimulation signal parameters may be related to food consumption (e.g. "consumption of a light meal" or "consumption of a heavy meal"). In some instances, it may be beneficial for the system (e.g., the algorithm) to accurately distinguish food-consumption-related versus food-consumption-unrelated physiological states, as this may improve therapy efficacy and/or may reduce the frequency and/or severity of unwanted side effects.

During the learning phase, the algorithm may be trained using the machine learning method by correlating values of physiological parameters with physiological states. In some variations, the machine learning method may be an artificial neural network, where the physiological parameters form input layer nodes, the physiological states form an output layer node, and the correlation weight values between the physiological parameters and the physiological states form the hidden layer nodes. The algorithm may calculate the correlation weights using one of the following classification methods: thresholding, multiple linear regression, k nearest neighbor, linear discriminant analysis, or support vector machines. In some embodiments, the algorithm may use an electrical circuit embedded in the implantable pulse generator, in the external programmer, and/or in another external device.

A clinician, a device company representative, and/or other member of authorized personnel may program the implantable pulse generator by setting up one or more stimulation programs for the patient and allowing the patient to adjust the stimulation parameters. Once the programs are established, the patient may have the ability to change only a subset of parameters in an individual program, e.g., only an amplitude, only a pulse width, or only a frequency. Also, at the initial setup, the clinician, the device company representative, and/or other member of authorized personnel may initialize the individual sensors with "normal" or expected values. In some variations, the clinician, the device company representative, and/or other member of authorized personnel may also set a confidence level for correlation weights in the algorithm, for example, from about 80% to about 99%, to indicate the end of the learning phase. The clinician, the device company representative, and/or other member of authorized personnel may also set a delta change threshold for individual sensors, e.g., 5-10% of the signal average, for detecting abnormal operations of the implantable pulse generator and/or sensor inputs that are outside an expected range, as described in more detail below.

During an embodiment of the learning phase, the individual sensors may be reset and normalized with initial values, and the implantable pulse generator may be instructed by a clinician, the device company representative, and/or other member of authorized personnel to initiate the learning phase of the algorithm. In the learning phase, the implantable pulse generator (e.g., via the algorithm) may continuously or intermittently monitor the patient's physiological parameters (e.g. autonomic nervous system parameters and intestinal activity parameters), may determine the physiological state (e.g. "food consumption" or "fasting"), and may adjust the stimulation parameters. In addition, the patient, the clinician, the device company representative, and/or other member of authorized personnel may change the stimulation program and/or the stimulation parameters.

In some variations of the learning phase, in response to the changed physiological state (e.g., provided by the patient), the algorithm may calculate current physiological parameters, determine the correlation weights with the patient-provided physiological state, and activate a preset or adjusted stimulation program or stimulation parameters. While recording the correlation weights, the algorithm may build a database of correlation weights between multiple physiological parameters and multiple physiological states and of preset and/or adjusted stimulation programs/parameters associated with particular physiological states.

In one example, the patient-provided physiological state may be "during heavy meal" and the measured physiological parameters may be: "LF power" is high and "HF power" is low. The implantable pulse generator may have been preprogrammed with a preset stimulation program, for example, Program 1, which corresponds to the physiological state "during heavy meal." Once this physiological state is detected (e.g., by receiving user input indicating this physiological state), the system may deliver Program 1. After an elapsed period of time, for example, two hours, the physiological state may have changed to, for example, "after heavy meal." The system may detect this change via patient reporting (e.g., the patient instructs the system that the physiological state has changed) or using preset time intervals for particular physiological states. For example, in some variations, the duration of particular states may be preset by a clinician, a device company representative, a patient, or the like. In the example described here, the duration of the physiological state "during heavy meal" may have been preset to two hours. At that time, the measured physiological parameters may be: "LF power" is medium and "HF power" is medium. The preset stimulation Program 1 may then be stopped. Although the stimulation may be stopped, the algorithm may continue to monitor for changes in physiological parameters, patient-provided physiological states, and/or patient adjustment of stimulation parameters.

The database of correlation weights and adjusted stimulation parameters for each physiological state may be continuously or intermittently populated and adjusted as the algorithm learns, while the clinician and patient are in full manual control of the stimulation programs and/or parameters. Referring again to the above example, if at any time the clinician or patient adjusts the parameters of Program 1 during the physiological state "heavy meal consumption", the algorithm may populate the database with the current physiological parameters, the physiological state "during heavy meal", and current Program 1 stimulation parameters (e.g., frequency, pulse width and amplitude). Over a period of time (e.g., 1 week, 2 weeks, 3 weeks, 1 month, 2 months, 1 week-3 weeks, 2 weeks-4 weeks, 1 month-2 months, or the like), the implantable pulse generator may collect sufficient data to meet the preset confidence levels for correlation weights and may enter the automatic operation phase.

In some variations, the learning phase may comprise sub-phases for certain physiological parameters (e.g. "LF power" and "HF power") and physiological states (e.g. "during heavy meal" and "after heavy meal"). For example, in some embodiments, the learning phase may comprise a first sub-phase, an autonomic nervous system sub-phase, and a second sub-phase, an intestinal activity sub-phase. In the autonomic nervous system sub-phase, the implantable pulse generator may utilize only the autonomic nervous system parameters (e.g. LF power, HF power, LF/HF ratio, as described above) for training (e.g., as input layer nodes) the algorithm. In the intestinal activity sub-phase, the implantable pulse generator may utilize the intestinal activity parameters (e.g., ISW frequency, ISW power, IB SN, intestinal temperature) in addition to the autonomic nervous system parameters for training the algorithm.

In some instances, the system may comprise a body-worn (i.e., not implanted) sensor (e.g., electrocardiographic electrode) to measure electrical activity of the heart (e.g., autonomic nervous system parameters). In these variations, the system may perform or begin to perform the autonomic nervous system sub-phase prior to implantation of the implantable pulse generator. For example, in one variation, the system may comprise a wearable electrocardiographic electrode, which may collect electrocardiographic data and send the data to the external programmer. This data may be used to train the algorithm module based on the autonomic nervous system parameters. In this variation, the external programmer, the computer, or the cloud server may initially comprise the algorithm module, which may later be transferred to the implantable pulse generator. In some instances, performance of the autonomic nervous system sub-phase prior to implantation may allow for an initial pre-selection of patients who may be suitable for implantation and/or may reduce the use of the battery of the implantable pulse generator (as it may only be used during the intestinal activity sub-phase).

During the automatic operation phase, the algorithm may use the information in the populated database to determine the physiological states and set the stimulation parameters, given certain combinations of physiological parameters. For example, when the implantable pulse generator detects a change in measured HRV parameters, (e.g., that "LF power"

is high and "HF power" is low), the algorithm may automatically determine the physiological state, (e.g., "during heavy meal"). As a result, the implantable pulse generator may automatically turn on the best-matching stimulation program or stimulation parameters determined during the learning phase, rather than using the initial stimulation parameters.

The length of time required to meet the confidence levels may be patient-dependent and may be influenced by one or more factors, including for example, the number and frequency of a clinician's and/or a patient's selections, and/or other factors that may vary for each patient depending on the patient's satisfaction level. Once the implantable pulse generator has met or exceeded the confidence levels, the algorithm may enter the automatic phase for that physiological state.

The implantable pulse generator need not enter the automatic operation phase for all physiological states simultaneously. In particular, the implantable pulse generator may enter the automatic operation phase for one physiological state but may remain in the learning phase for one or more other physiological states. Put another way, the confidence level for correlation weights between all physiological parameters and all physiological states need not be achieved before the device can enter the automatic operation phase for a certain physiological state. As an example, if the algorithm reaches the preset confidence level for the correlation weights to determine the physiological states "during heavy meal" and "after heavy meal", then the implantable pulse generator may proceed into the automatic operation phase for these states only, while the device may continue to operate in the learning phase for other physiological states.

When the implantable pulse generator enters the automatic operation phase (and optionally in the learning phase), it may automatically change the stimulation program and/or stimulation parameters for the patient. In some variations, the system may alert the patient before automatically making an adjustment by, for example, displaying a message, illuminating a status light, or producing a discrete vibration on an external programmer, a combination thereof, or the like. In some variations, this alert feature may be switched-off, removed over time, or eliminated entirely.

The implantable pulse generator may continuously or intermittently check for a change in one or more measured physiological parameters, a change in stimulation program, and/or a change in stimulation parameters that are outside the preset delta change thresholds. If such a change is detected and is outside the delta change thresholds, in certain embodiments, the implantable pulse generator may alert the patient that such a change has occurred. In certain cases, the system may notify the clinician directly by sending an automatic note (e.g. email, text message, or otherwise as appropriate) of the change in the physiological parameters and/or stimulation parameters. For example, such a change may include a physiological parameter value or a patient-adjusted amplitude that is outside preset delta change thresholds. In response, the patient may override this alert, and the algorithm may record the event as a new database entry and start to learn more about this physiological parameter and/or stimulation parameter. In other embodiments, the patient may turn off the stimulation therapy and see a clinician. The clinician may then troubleshoot and adjust the therapy for the patient. The implantable pulse generator may re-enter the learning mode for these physiological parameters and/or stimulation parameters.

Signal Delivery Devices

Referring back to FIG. 1, the system 100 may comprise a signal delivery device 112 that may be electrically coupled to the implantable pulse generator 101. The signal delivery device 112 may be used to apply a stimulation signal to the muscle of the patient's small intestine. In some embodiments, the signal delivery device 112 may comprise a lead electrode 103 with a plurality of contacts. In some variations, the contacts may be platinum contacts. In some embodiments, the sensor 116 may also be located on the lead electrode 103. In certain further embodiments, the same contacts in the lead electrode 103 may be used for both sensing and signal delivery. For example, when placed in the small intestine of a patient, the contacts of the lead electrode 103 may be used as both a myoelectrical sensor and for delivery of electrical stimulation therapy. Put another way, in some embodiments, the same electrode may function as the lead electrode 103 and as the sensor 116.

In some embodiments, the signal delivery device 112 may comprise a lead electrode 103 that may be permanently implanted (e.g., surgically) in the intestinal wall and may be electrically coupled to the implantable pulse generator 101 using a lead 102. In other embodiments, the signal delivery device 112 may comprise a lead electrode 103 that may be temporarily placed in the intestinal lumen using a non-surgical approach, such as, for example, a trans-nasal or trans-oral catheter. In these embodiments, the lead electrode 103 may be electrically coupled to an externally placed pulse generator, and may be used for temporary therapy and/or for screening patients during a screening phase, as will be described in more detail herein.

Figure 10A:
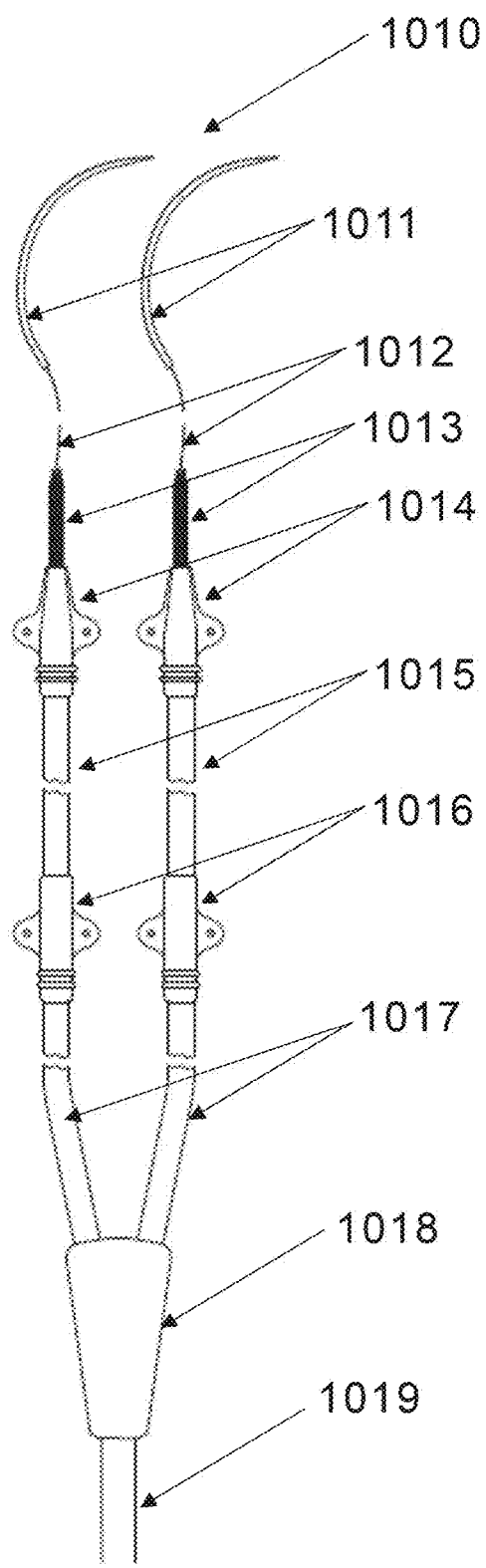
FIGS. 10A-10B depict illustrative variations of signal delivery devices that may be used for one or both of signal delivery and sensing.

FIG. 10A depicts a variation of a distal portion of a signal delivery device 112 that may be used for one or both of signal delivery and sensing (e.g, for sensing any of the cardiac and/or intestinal data described herein such as electrocardiographic data, myoelectrical intestinal activity data, intestinal temperature data). As shown there, the signal delivery device 1010 may comprise an elongate body 1019 coupled to a bifurcation junction 1018, which couples the elongate body 1019 to two electrode assemblies. Each lead electrode assembly may comprise a tunneling needle 1011 at the distal end, which may be coupled to an electrical contact 1013 via a non-absorbable (e.g., polypropylene, nylon, polybutester) or an absorbable (e.g. polyglycolic acid, polylactic acid, polydioxanone, caprolactone, vicryl) suture 1012. Each electrical contact 1013 may be coupled to a distal tissue anchor 1014, which may be coupled to a distal lead body 1015. Each distal lead body 1015 may be coupled to a proximal tissue anchor 1016, which in turn may be coupled to a proximal lead body 1017. Each of the proximal lead bodies 1017 may merge in the bifurcation junction 1018 to form a single elongate body 1019. The elongate body 1019 may couple the electrode assemblies to the implantable pulse generator 101 and/or to a trans-nasal or a trans-oral catheter.

Figure 10B:
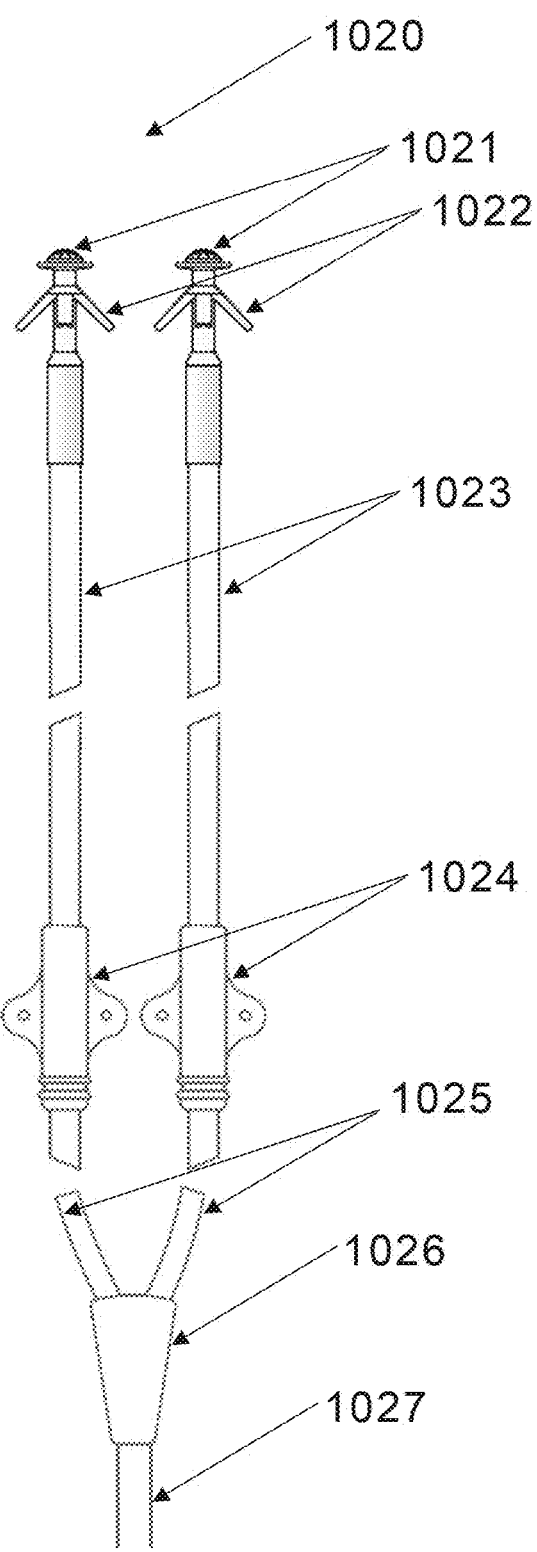

FIG. 10B depicts another embodiment of a distal portion of a signal delivery device 112 that may be used for both signal delivery and sensing (e.g, for sensing any of the cardiac and/or intestinal data described herein such as electrocardiographic data, myoelectrical intestinal activity data, intestinal temperature data). As shown there, the signal delivery device 1020 may comprise an elongate body 1027 coupled to a bifurcation junction 1018, which couples the elongate body 1027 to two electrode assemblies. Each electrode assembly may comprise an electrical contact 1021 at the distal tip, which may be coupled to a distal tissue anchor 1022. The distal tissue anchor 1022 may be any suitable tissue anchor, and in some variations, may comprise one or more times (e.g., two, three, four, or more). Each distal tissue anchor 1022 may be coupled to a distal lead body 1023, which may be coupled to a proximal tissue anchor 1024. Each proximal tissue anchor 1024 may be coupled to a proximal lead body 1025, and the two proximal lead bodies 1025 may merge in the bifurcation junction 1026 to form a single elongate body 1027. The elongate body 1027 may couple the electrode assemblies to the implantable pulse generator 101 and/or to a trans-nasal or trans-oral catheter.

The electrode assemblies depicted in FIGS. 10A and 10B each comprise an electrical contact 1013, 1021. The electrical contact 1013, 1021 may comprise a contact surface made from a biocompatible metal (e.g., stainless steel, gold, platinum, iridium, iridium oxide, titanium), a metal alloy (e.g., MP35N), and/or a conductive polymer, and may be used to deliver electrical current to tissue (e.g., intestinal tissue). The proximal and distal lead bodies 1015, 1017, 1023, and 1025, and/or the elongate bodies 1019, 1027 may comprise a core of electrically conductive wires made from metal (e.g., stainless steel, platinum, silver, iridium, nickel, cobalt), a metal alloy, and/or a conductive polymer. The wires may be surrounded by an insulating layer or jacket, which may be made from a flexible dielectric material (e.g., polyurethane, parylene, or silicone). The proximal and distal anchors 1014, 1016, 1022, and 1024 may be made from a dielectric material (e.g., polyurethane, parylene, or silicone) and may be used to attach the electrode assemblies (e.g., the electrical contacts 1013, 1021, lead bodies 1015, 1017, 1023, 1025) to a patient's tissue (such as muscle tissue) and to limit or otherwise prevent it from moving (e.g., swaying or back-and-forth).

It should be appreciated that the systems described herein may comprise a plurality of signal delivery devices 112, such as, for example, those depicted in FIGS. 10A-10B. In some variations, the systems may comprise one or more (e.g., 2, 3, or more) of the signal delivery devices 1010 depicted in FIG. 10A and/or one or more (e.g., 2, 3 or more) of the signal delivery devices depicted in FIG. 10B. Additionally or alternatively, in some variations, the signal delivery devices 112 depicted in FIGS. 10A and 10B may be and/or may comprise a cardiac sensor (e.g., electrocardiographic electrode) or an intestinal sensor (e.g., intestinal myoelectrical electrode and/or intestinal thermal probe).

External Programmer

The system 100 may also comprise an external programmer 104 that may be configured to communicate with and/or control the implantable pulse generator 101. As shown in FIG. 1, the external programmer 104 may comprise a housing 105 carrying multiple input devices 106 (e.g., push buttons, track wheels, directional keys, etc.), a display 107 (e.g., a liquid crystal display). The external programmer 104 may also comprise internal circuitry (not shown) that may be configured to create a bidirectional wireless data link 109 to communicate with the pulse generator 101 and to adjust its operation (e.g., by changing a stimulation program and/or one or more stimulation parameters). In certain embodiments, the external programmer 104 may be configured as a handheld device. In other embodiments, components of the external programmer 104 may have other portable configurations. For example, the external programmer 104 or components thereof may be mounted on a band, strap, or belt, that maybe worn around a patient's wrist, arm, hand, finger, head, forehead, neck, ankle, torso, chest, or waist. In some instances, the external programmer 104 or components thereof may be mounted to attach to a patient's clothing (e.g., via a clip, pin, or the like), may be shaped like earphones or glasses such that they may be worn in a patient's ears or on a patient's face, or may be incorporated within a hand-held computing device (such as a laptop computer, a notebook computer, a tablet computer, a PDA, a smart phone, or a smart watch). In some variations, the external programmer 104 may be omitted and a computer may establish a bidirectional wireless data link to communicate with the implantable pulse generator 101.

Charging Antenna

In some instances, the system 100 may also comprise a wireless charging antenna 108 that may electrically couple with the pulse generator 101 to charge the pulse generator 101 while implanted. The wireless charging antenna 108, which, in some variations, may comprise an induction coil, may create a wireless power communication link 115 to the pulse generator 101 for re-charging the battery 124 of the pulse generator 101.

Computer

In some embodiments, the therapy system 100 may also comprise a computer 110. The computer 110 may be coupled to the external programmer 104 via a bidirectional wireless data link 111 (e.g., a Wi-Fi link, a Bluetooth link, an NFC link, etc.). In some variations, the computer 110 may be coupled to a cloud server 114 via a bidirectional network connection 113 (e.g., an Internet connection, an intranet connection, or the like). In some instances, the computer 110 and/or the cloud server 114 may be omitted. It should be appreciated that the systems described herein may also comprise other suitable network components, for example, routers, switches, data storage centers, or the like.

The computer 110 may comprise one or more processors, tangible memories (e.g., random access memories (RAMs), read-only memories (ROMs), and/or programmable read only memories (PROMS)), tangible storage devices (e.g., hard disk drives, CD/DVD drives, and/or flash memories), system buses, video processing components, network communication components, input/output ports, and/or user interface devices (e.g., keyboards, pointing devices, displays, microphones, sound reproduction systems, and/or touch screens).

The computer 110 may be a desktop computer or a portable computer, such as a laptop computer, a notebook computer, a tablet computer, a PDA, a smart phone, a smart watch, or part of a larger system, such a vehicle, appliance, and/or telephone system.

The computer 110 may comprise software (e.g., one or more operating systems, device drivers, application programs, and/or communication programs). In some variations, the software may comprise programming instructions and may include associated data and libraries. When included, the programming instructions may be configured to implement one or more algorithms that implement one or more of the functions of the computer system, as recited herein. The description of each function that is performed by each computer system also constitutes a description of the algorithm(s) that performs that function.

The software may be stored on or in one or more non-transitory, tangible storage devices, such as one or more hard disk drives, CDs, DVDs, and/or flash memories. The software may be in source code and/or object code format. Associated data may be stored in any type of volatile and/or non-volatile memory. The software may be loaded into a non-transitory memory and executed by one or more processors.

Methods

Methods for delivering a stimulation signal or stimulation program to tissue (e.g., an intestinal muscle such as intestinal muscle of the duodenum, the jejunum, or the ileum) of a patient may generally comprise measuring electrical activity of the heart using one or more cardiac sensors, measuring intestinal activity (e.g., electrical, thermal) using one or more intestinal sensors, receiving the measured data from the cardiac and intestinal sensors, calculating one or more physiological parameters from the data using, for example, the calculation methods described herein, determining and/or recording a physiological state of the patient using the physiological parameters, adjusting the value of a stimulation parameter of a stimulation signal, and instructing the implantable signal delivery device 112 to apply a stimulation signal comprising the adjusted stimulation parameter. In some variations, the methods may comprise automatically starting or stopping stimulation based at least in part on the determined physiological state.

Methods may further comprise surgically implanting the implantable pulse generator 101. Surgically implanting the implantable pulse generator 101 may comprise placing the implantable pulse generator 101 in a subcutaneous pocket in the abdomen or lower back region, routing the lead 102 toward the small intestine, and placing the lead electrode 103 in the serosa of the small intestine via open surgery, endoscopic, or laparoscopic surgery. The lead electrode 103 may be placed in different parts of the small intestine, such as, in the duodenum, the jejunum, or the ileum. The surgical implantation may be performed under general anesthesia and a hospital stay may or may not be required.

In some variations, the methods described here may comprise a non-surgical screening phase, during which temporary therapy may be delivered to a patient (e.g., a patient suffering from a chronic intestinal or metabolic disorder). The screening phase may occur before implantation of one or more system components (e.g., the implantable signal delivery device 102 and/or an implantable pulse generator 101) for treatment during a chronic treatment phase. In these variations, a temporary signal delivery device may be non-surgically positioned and an external pulse generator may be utilized to assess the suitability of a patient for the intestinal stimulation therapy. A physician may perform one or more initial or baseline tests before delivering temporary therapy during the screening phase and may perform one or more of the same tests during and/or at the end of the screening phase to evaluate the efficacy of the temporary therapy. For example, a physician may preform one or more tests (e.g., Cardiovagal Test, Heart Rate Variability Test, Sympathetic Skin Response, Valsalva Maneuver, Tilt Table Test, Gastric Emptying Test, Quantitative Sudomotor Axon Reflex Test, Thermoregulatory Sweat Test, Urodynamic Test) to evaluate the autonomic nervous system function, administer one or more tests (e.g., myoelectrical intestinal recording, electrogastrography, Oral Glucose Tolerance Test, Insulin Tolerance Test, gastroduodenal manometry, intestinal endoscopy, calprotein and blood in stool (feces), metabolic biomarkers in blood) to evaluate the intestinal activity. The physician or care provider may perform the tests before the temporary therapy and during, and/or after the temporary therapy. If it is determined, based on the results of the screening phase, that extended intestinal stimulation therapy is likely to be efficacious for a patient, the patient may progress to the treatment phase, in which one or more system components may be surgically implanted as described above. However, if it is determined that extended intestinal stimulation therapy is unlikely to be efficacious, or that the efficacy of the extended therapy is outweighed by the risks and/or cost associated with surgical implantation of one or more components of the system, the patient may not progress to the treatment phase and may therefore avoid the cost and health risks associated with the implantation surgery and extended therapy. The screening phase may be any length suitable to determine appropriateness of extended intestinal stimulation therapy and may be, for example, between about 3 days and about 60 days (e.g., 14 days), including all values and sub-ranges therein.

During the screening phase, the temporary signal delivery device may be positioned non-surgically. For example, the temporary signal delivery device may be attached to a trans-nasal or a trans-oral catheter to deliver intraluminal intestinal electrical stimulation (e.g., a screening stimulation signal). Methods of placing the temporary signal delivery device may comprise inserting a trans-nasal or trans-oral catheter with the temporary signal delivery device and advancing the distal end toward and into the duodenum. The non-surgical catheter insertion may be performed without anesthesia or under local anesthesia, and a hospital stay may not be required. Once the catheter with temporary signal delivery device has been inserted, accurate placement of the device may be confirmed, by, for example, applying electrical stimulation at a level above the threshold for activation of either the sensing fibers or the motor fibers in the intestinal wall resulting in detectable twitching of the intestinal muscle.

The temporary signal delivery device may be left inserted and connected to an external pulse generator for the length of the screening phase. For example, in some variations, a catheter with temporary signal delivery device may be used for between about one hour and 21 days (e.g., 8 hours), after which it may be removed and later replaced with another catheter with temporary signal delivery device. In some embodiments, the catheter with temporary signal delivery device may be removed after each stimulation session during the screening phase and a new catheter with temporary signal device may be inserted at the next stimulation session. The stimulation applied using the temporary signal delivery device may be applied continuously or intermittently after each meal (e.g., for 1 to 4 hours). The temporary stimulation may be delivered at a stimulation amplitude of about 0.1 mA to about 30 mA while keeping the amplitude below the threshold for activation of the sensory and motor fibers in an intestinal wall (e.g. 90% of the threshold), at a pulse width of about 20 microseconds to 100 milliseconds, including all values and subranges therein (e.g. about 4 milliseconds, from about 1 millisecond to about 5 milliseconds, from about 1 millisecond to about 10 milliseconds), at a frequency of about 0.01 to about 50 Hz (e.g. about 0.2 Hz, from about 0.01 Hz to about 1 Hz, from about 0.01 Hz to about 5 Hz), and at a duty cycle of from about 0.1% to about 50%, including all values and subranges therein (e.g. about 10% with 10 sec ON and 90 sec OFF, less than about 10%, from about 0.1% to about 5%, from about 0.1% to about 10%). One or more of the stimulation parameters of the stimulation delivered using the temporary signal delivery device during the screening phase (e.g., a screening stimulation) may be the same as, or different from, one or more of the stimulation parameters of the stimulation delivered during the treatment phase.

Initial setup may begin before, during, or after implantation using an external programmer. In some variations, initial setup may occur soon after implantation. During the initial setup, a clinician or device representative may set the initial stimulation parameters, the initial correlation weights between the physiological parameters and the physiological states, and the initial correlation weights between the physiological states and the stimulation parameters for the algorithm. For example, in one embodiment, an initial correlation weight may comprise a weight between the first amplitude and a first physiological state (e.g., "during light meal") and a weight between a second amplitude and a second physiological state (e.g., "during heavy meal"). In some variations, stimulation parameters may be initially set by the clinician with the patient's feedback. This may occur while the algorithm is in the learning phase. As mentioned above, during the automatic operation phase, the pulse generator 101 may automatically determine the physiological state and the stimulation parameters.

During the learning phase, the weights may be adjusted based on feedback from a clinician or the patient, who may be periodically entering the stimulation parameters and physiological states within the preset values selected at or shortly after implantation using an external programmer 104. The clinician, the device company representative, and/or other member of authorized personnel may also set a confidence level to indicate the end of the learning phase for the algorithm for example, from about 80% to about 99%. Once the implantable pulse generator has collected sufficient data to meet the set confidence levels for setting the correlation weights, the implantable pulse generator 101 may automatically enter the automatic operation phase. In the automatic operation phase the implantable pulse generator may automatically determine a patient's physiological state, and may automatically adjust the stimulation parameters for the signal delivery device 112 in response to a change in the physiological parameters (autonomic nervous system parameters and intestinal activity parameters). This may result in an improvement and/or maintenance of treatment efficacy, without further input from the patient.

During the learning phase, the implantable pulse generator 101 may continuously or intermittently monitor the sensor data from the sensor 116 and the stimulation parameters from the external programmer 104, extract and/or calculate the physiological parameters (autonomic nervous system parameters and intestinal activity parameters) and/or adjust the stimulation parameters. In certain embodiments, the implantable pulse generator 101 may detect a change in at least one stimulation program or a stimulation parameter (e.g., an amplitude and/or a frequency of stimulation). For example, the patient may increase or decrease the amplitude of the applied therapy signals using the external programmer 104, and the implantable pulse generator 101 may record the amplitude adjustment and send the adjusted stimulation pulses to the signal delivery device 112.

When the implantable pulse generator 101 detects a change in the sensor data or the physiological parameters, the pulse generator 101 may calculate all or a subset of the current physiological parameters (e.g. autonomic nervous system parameters and intestinal activity parameters). In certain embodiments, the physiological parameters may be calculated using time-domain calculation methods, such as the arithmetic mean, harmonic mean, quadratic mean, weighted mean, median, geometric median, maximum, minimum, standard deviation (root mean square), area under the curve, peak-to-peak interval, Nonlinear Energy Operator, Shannon entropy, and/or Fisher entropy. In some embodiments, the physiological parameters may be calculated using frequency-domain calculation methods, such as Fast Fourier Transform, Hilbert Transform, Spectral entropy, high-pass filtering, low-pass filtering, band-pass filtering, and/or power of the frequency band.

The memory module 122 in the implantable pulse generator 101 may include or communicate with the algorithm module 126 containing the algorithm. The algorithm may be used in a read-and-write mode during the learning phase. Once the learning phase is completed, the algorithm may be used in a read-only mode for the automatic operation phase. In the learning phase, the algorithm may collect sensor data, calculate the physiological parameters, correlate the patient-provided physiological state with calculated physiological parameters, and correlate the physiological state with present or patient-adjusted stimulation parameters. In the automatic operation phase, the algorithm may receive sensor data, calculate the physiological parameters, determine the physiological state, and automatically set the stimulation parameters based on the correlation established during the learning phase.

In certain embodiments, the duration of the learning phase may be predetermined (e.g., 1 week, 1-2 weeks, 1-3 weeks, 1-4 weeks, 2-4 weeks, 2-5 weeks, 1-10 weeks or longer) and may be set by the clinician, the device company representative, and/or other member of authorized personnel. In other embodiments, the duration of learning phase may be variable. For example, in some variations, the duration of the learning period may be determined using the preset confidence levels for the correlation weights stored in the implantable pulse generator 101. In these variations, the learning phase may terminate when the correlation weights for certain physiological states (e.g. "during heavy meal" and/or "after heavy meal"), have reached a specified or predetermined confidence level, for example, from about 80% to about 99%. In some variations, the patient and/or the clinician may terminate the learning phase irrespective of an elapsed time or current confidence level of the correlation weights, and/or may reset the implantable pulse generator 101 with initial settings. In some variations, the duration of the learning phase may be predetermined based on, for example, a patient's demographic and/or health conditions.

Once the physiological states and corresponding stimulation parameters are established (e.g., once the learning phase is completed), the implantable pulse generator 101 may automatically start, stop, or adjust the stimulation parameters based on the sensed measurements and calculated or determined physiological state. For example, when the implantable pulse generator 101 receives sensor readings that indicate a food consumption state (e.g., "during light meal", "during heavy meal"), the implantable pulse generator 101 may automatically increase a stimulation parameter (e.g., an amplitude) based on a corresponding value of the initial or patient-adjusted amplitude in the database for that food consumption state. In this variation, the patient need not manually operate the external programmer 104 in order to adjust the applied stimulation parameters. As a result, the therapy system 100 may be less cumbersome, time-consuming, and/or restrictive to operate than conventional systems.

In some variations, the implantable pulse generator 101 may gradually adjust the stimulation parameters. For example, once the implantable pulse generator 101 determines that a patient is in a physiological state of "consuming a light meal", the implantable pulse generator 101 may instruct the signal delivery device 112 to apply a first stimulation signal. If the implantable pulse generator determines that the patient's physiological state has changed to "consuming a heavy meal", the implantable pulse generator 101 may instruct the signal delivery device 112 to gradually apply a second (e.g. larger amplitude) stimulation signal. In this variation, the second stimulation signal may be applied with a gradual ramp-up. In some variations, instead of establishing individual stimulation parameters for each physiological state, the system may provide gradually increasing or decreasing stimulation levels for a specific sequence of physiological states. After the learning phase is completed, the implantable pulse generator 101 may continue measuring and storing the current values of physiological parameters, determined physiological state, and generated stimulation parameters, as described above. The implantable pulse generator 101 may periodically (e.g., daily, weekly, biweekly, or the like) or continuously update (e.g., refine) the correlation weights based on these new measurements. In other embodiments, the process of further updating the correlation weights may be omitted.

In some embodiments, the implantable pulse generator 101 may alert a patient and/or clinician if a change is detected in one or more of the physiological parameters. For example, if the implantable pulse generator 101 detects a large change (e.g., 10%, 20%, 30%, 40%, between 10%-20%, between 20%-30%) in one or more of the physiological parameters, the implantable pulse generator 101 may output an alarm to the patient and/or the clinician indicating that an additional assessment is needed. In some variations, the patient and/or the clinician may decide when to reestablish the physiological states based on changes in the patient's disease conditions, such as a progression of treated disease or appearance/disappearance of other diseases or medical conditions.

Algorithm

Figure 4:
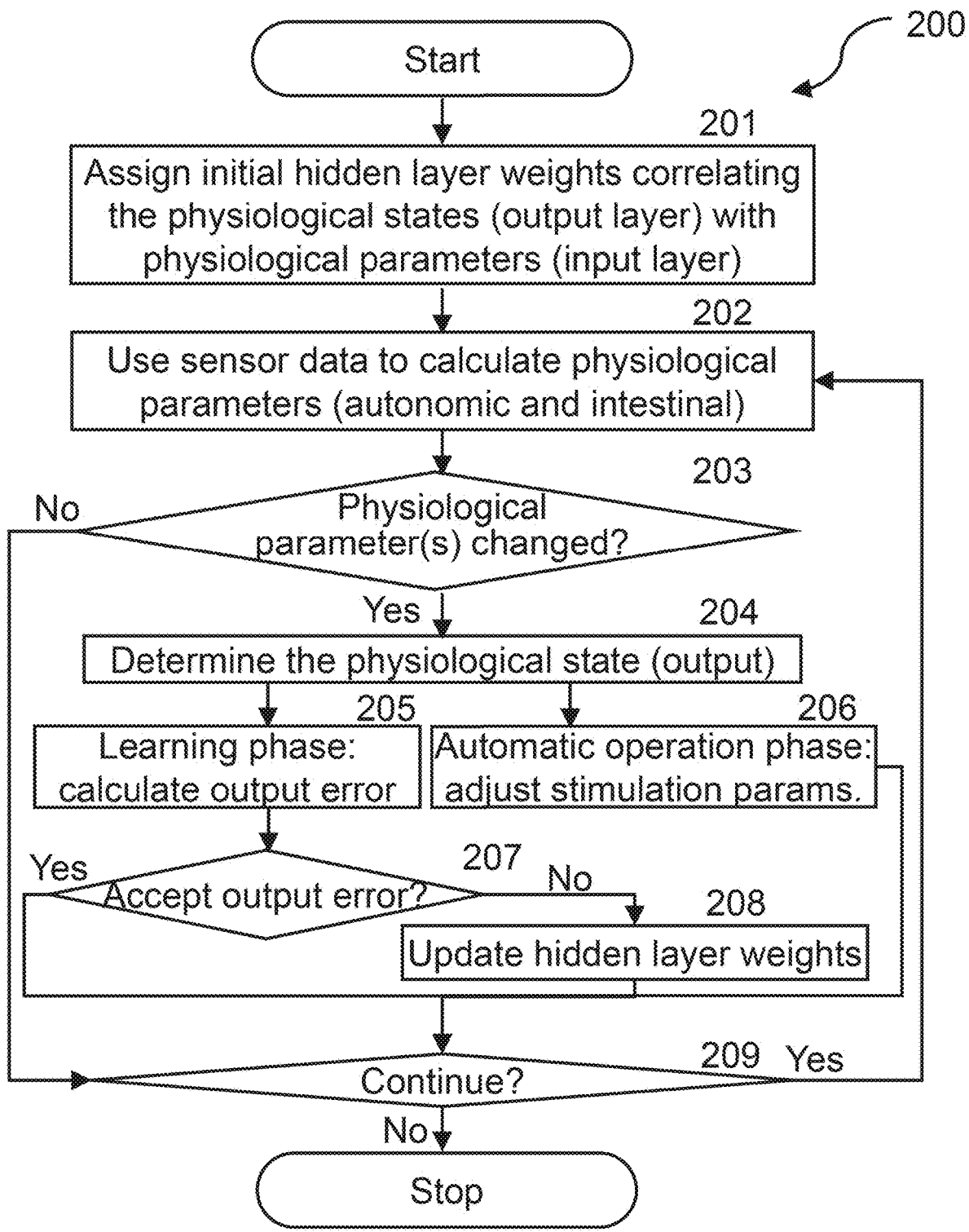
FIG. 4 is a flow diagram depicting a variation of a method for providing adjusted stimulation signals.

FIG. 4 is a flow diagram describing the steps of the learning and automatic phases of the algorithm 200 of the systems described here. The algorithm 200 depicted in FIG. 4 may allow the system to automatically adjust the stimulation signals delivered to the intestinal muscle tissue based on the calculated physiological parameters (autonomic and intestinal) and on the physiological states (e.g., patient-provided or determined). In the illustrated embodiment, the algorithm 200 uses a particular machine learning technique, the artificial neural network (ANN). Use of the algorithm depicted in FIG. 4 may reduce or eliminate the need for the patient to interact with the external programmer in the automatic operation phase.

Generally, the algorithm 200 depicted in FIG. 4 may comprise assigning initial hidden layer weights correlating the physiological states (output layer) with physiological parameters (input layer), using the data from sensors (e.g. electrocardiographic sensor and intestinal myoelectrical sensor) to calculate physiological parameters (autonomic and intestinal) (202), and determine whether one or more physiological parameters have changed above a delta change threshold (203). If the change in the physiological parameter is at or above a preset delta change threshold (e.g., 5-10% of the average), the algorithm 200 may further comprise calculating the physiological state (output) (204).

The next step in the algorithm 200 depicted in FIG. 4 depends on the current phase of the algorithm 200, i.e., whether the algorithm is in the learning phase or the automatic operation phase. During the learning phase, the algorithm 200 may calculate the output error between the determined physiological state and the patient-provided physiological state (205) and evaluate whether the output error is acceptable (207). In one embodiment, the evaluation is based on thresholding, with thresholds such as 10%, 15%, 20%, 10-20%, or 15%-20%. In different embodiments, other classification methods may be used, such as, for example, multiple linear regression, k nearest neighbor, linear discriminant analysis, or support vector machines. If the output error is above the acceptable level, the algorithm 200 may update the hidden layer weights based on the new correlations between the physiological state classifications (output layer) with physiological parameters (input layer) (208). The ANN database of physiological parameters (input layer), the weights (hidden layer), and the physiological states (output layer) may be updated as needed and stored in the memory module 122. During the automatic operation phase, instead of calculating the output error, the algorithm 200 may automatically adjusting the stimulation parameters, such an amplitude, a frequency, an electrode contact arrangement, and/or other suitable stimulation parameters, (206) based on determining a new physiological state (204). In some variations, the algorithm 200 may stop when the correlation weights reach or exceed the preset confidence level (209). In some instances, the algorithm 200 may also be stopped and/or restarted manually by a clinician based on changes in patient's disease conditions.

In some embodiments, the system may provide (e.g., via the implantable pulse generator, via a computer) a warning signal to the patient indicating that the ANN update has been performed and/or that a clinician should perform a checkup. The clinician may then determine whether the signal delivery device 112 (FIG. 1) requires any physical adjustment. If so, the clinician may readjust the signal delivery device 112 and restart the algorithm at the step of assigning initial hidden layer weights (201).

In some variations, the algorithm described here may be implemented without a clear distinction between the learning phase and the automatic operation phase. Instead, both phases may be executed simultaneously. For example, in these variations, the method may comprise tracking the physiological parameters for a sliding period of time (e.g., 1 week, 2 weeks, 1-2 weeks, or more), while continuously or intermittently updating the correlation weights between physiological parameters and physiological states (205) and the patient-adjusted stimulation parameters (206). For example, if the patient manually overrides the preset stimulation parameters for a particular physiological state, the algorithm may update the correlation weight with the patient selection. The weight adjustment may depend on the frequency with which each stimulation parameter is selected and/or the duration of use for each stimulation parameter. In other embodiments, the weights may be adjusted in other ways. For example, in some variations, the most recent patient selection may receive the highest weight.

Figure 5:
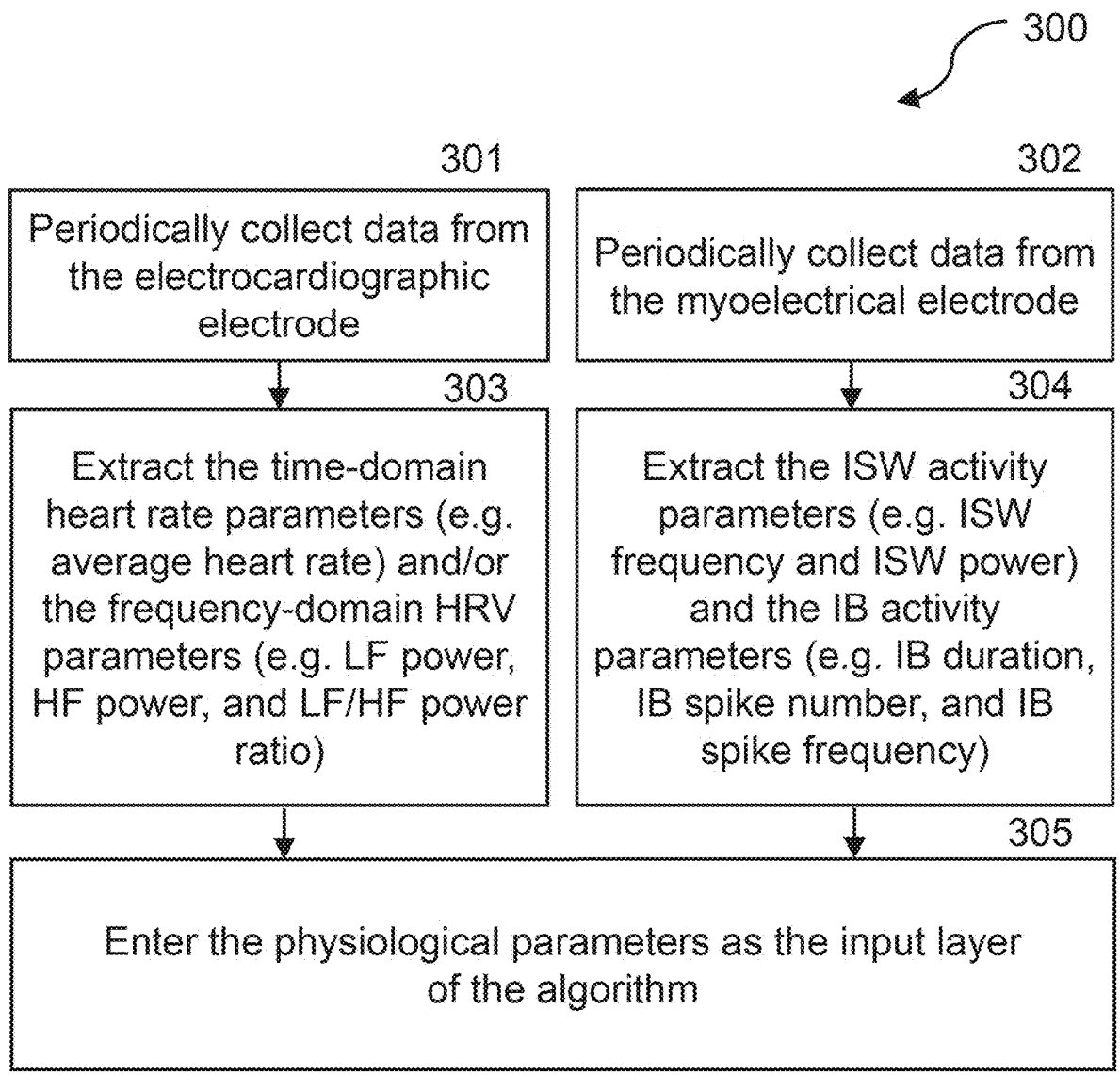
FIG. 5 is a flow diagram depicting an exemplary process for tracking incoming data for physiological parameters.

FIG. 5 is a flow diagram illustrating a method for measuring or receiving and processing autonomic nervous system data from a first sensor (e.g., an electrocardiographic sensor) and/or intestinal activity data from a second sensor (e.g., a myoelectrical intestinal sensor, an intestinal thermal probe) for use in the stimulation methods and systems described here. In particular, FIG. 5 depicts a flow diagram illustrating a method for collecting data for the physiological parameters (300) based on the time-domain and frequency-domain heart rate parameters, the ISW activity parameters, and the IB activity parameters. As shown there, the method (300) may comprise collecting data, e.g., periodically, from a first sensor (e.g., an electrocardiographic electrode) (301), extracting the heart rate parameters including, for example, time-domain heart rate parameters such as average heart rate and/or the frequency-domain HRV parameters such as LF power, HF power, and the LF/HF power ratio (303) from the collected data, and using the extracted heart rate parameters to deliver, control, and/or adjust stimulation delivery (e.g., by entering the heart rate parameters as the input layer of the algorithm) (305).

Additionally or alternatively, the method (300) may comprise collecting data, e.g., continuously or intermittently, from a second sensor (302). The second sensor may be an intestinal sensor, for example, an intestinal myoelectrical electrode or intestinal temperature sensor. The method (300) may further comprise extracting the ISW activity parameters (e.g. ISW frequency and ISW power) and the IB activity parameters (e.g. IB duration, IB spike number, and IB spike frequency) (304) from the collected data, and using the extracted parameters to deliver, control, and/or adjust stimulation delivery (e.g., by entering the ISW activity parameters and/or the IB activity parameters as the input layer of the algorithm) (305).

Accordingly, the method (300) may comprise collecting data from both a first sensor (e.g., a cardiac sensor such as an electrocardiographic electrode) and a second sensor (e.g., an intestinal sensor such as an intestinal myoelectrical electrode and/or an intestinal temperature sensor), extracting the time-domain heart rate parameters and/or the frequency-domain HRV values from the data from the first sensor, extracting the ISW activity parameters and the IB activity parameters or intestinal temperature from the data from the second sensor, and utilizing one or more of the extracted parameters to determine a physiological state and ultimately deliver, control, and/or adjust stimulation signal delivery. In variations in which additional sensors are utilized, data from each sensor may be collected, the relevant parameters may be extracted, and one or more of the parameters may be utilized to determine a physiological state and ultimately deliver, control, and/or adjust stimulation signal delivery. For example, in a variation in which an electrocardiographic electrode, a myoelectrical electrode, and an intestinal thermal probe are utilized, the method may comprise extracting the time-domain heart rate parameters and/or the frequency-domain HRV values from the data from the electrocardiographic electrode, extracting the ISW activity parameters and the IB activity parameters from the data from the myoelectrical electrode, extracting the intestinal temperature from the data from the intestinal thermal probe, and utilizing one or more of the extracted parameters to determine a physiological state and ultimately deliver, control, and/or adjust stimulation signal delivery.

Figure 6:
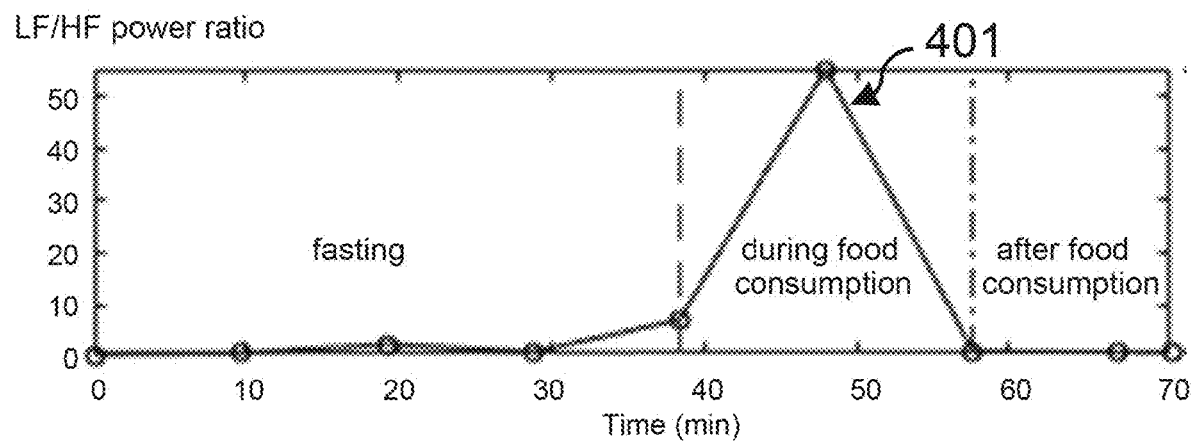
FIG. 6 graphically illustrates the use of frequency-domain heart rate variability parameters extracted from electrocardiographic data, and particularly the power ratio of the low frequency and high frequency bands, during fasting, during food consumption, and after food consumption.

FIG. 6 illustrates the use of frequency-domain HRV parameters calculated from the electrocardiographic data, and particularly the LF/HF power ratio. FIG. 6 depicts the change in the LF/HF power ratio over time, and in particular, illustrates how the LF/HF power ratio changes before, during, and after food consumption. During fasting, the LF/HF power ratio is very low and relatively constant. The LF/HF power ratio is increased immediately after the initiation of food consumption and is decreased to a low level soon after completing food consumption. The LF/HF power ratio, therefore, has a good predictive value for distinguishing the physiological state "during food consumption" from two other states: "fasting" and "after food consumption". This may be reflected in a high correlation weight between the physiological parameter "LF/HF power ratio" and physiological state "during food consumption", while the correlation weights between the physiological parameter "LF/HF power ratio" and physiological states "fasting" and "after food consumption" may be low. This illustrates how the correlation weights for HRV parameters may be adjusted during the learning phase of the algorithm operation.

Figure 7:
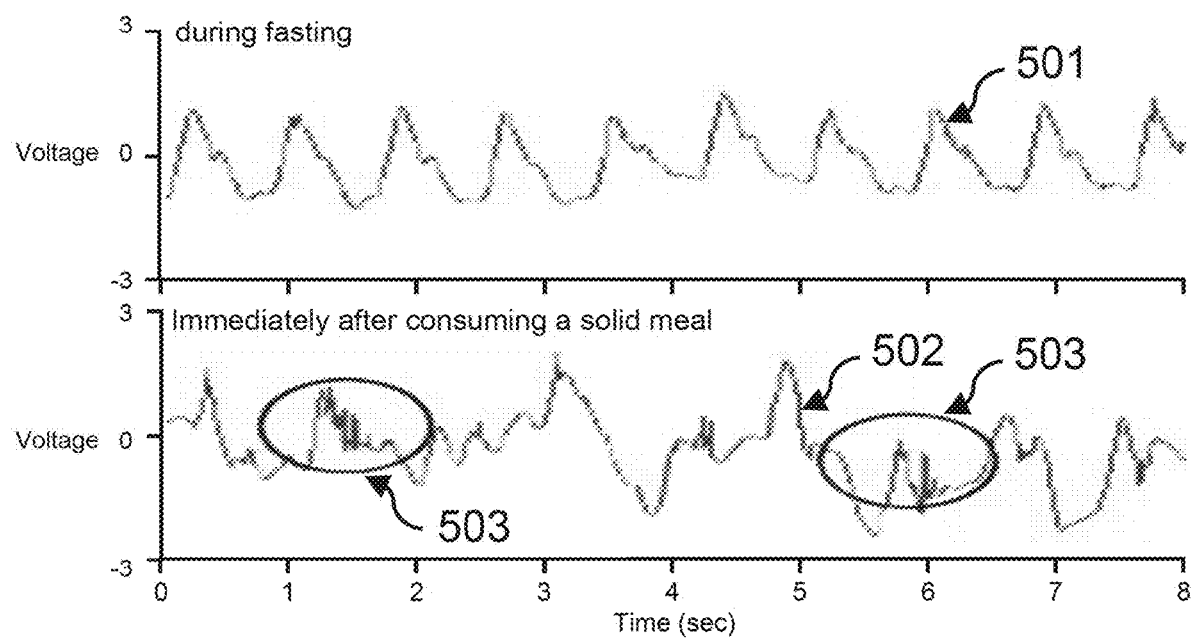
FIG. 7 graphically illustrates myoelectrical activity data collected with a myoelectrical sensor for calculating the intestinal slow wave activity parameters.

FIG. 7 illustrates the use of myoelectrical activity data collected with a myoelectrical intestinal sensor (e.g., a myoelectrical electrode) for calculating the ISW activity parameters (e.g. ISW frequency and ISW power) and the IB activity parameters (e.g. IB duration, IB spike number, and IB spike frequency). FIG. 7 depicts the change in the measured voltage over time collected during the fasting physiological state (501) and after consuming a solid meal (502). Immediately after consuming a solid meal, the ISW frequency is decreased, the ISW inter-wave interval and the ISW amplitude are increased, and the IB activity has emerged (503). The physiological parameters "ISW frequency", "ISW inter-wave interval", "ISW amplitude", and "IB duration", therefore, have a good predictive value for distinguishing the physiological states "during solid meal consumption" and "fasting", which may be reflected in a high correlation weight between these physiological parameters and physiological states. This illustrates how the correlation weights for ISW and IB parameters may be adjusted during the learning phase of the algorithm operation.

Figure 8:
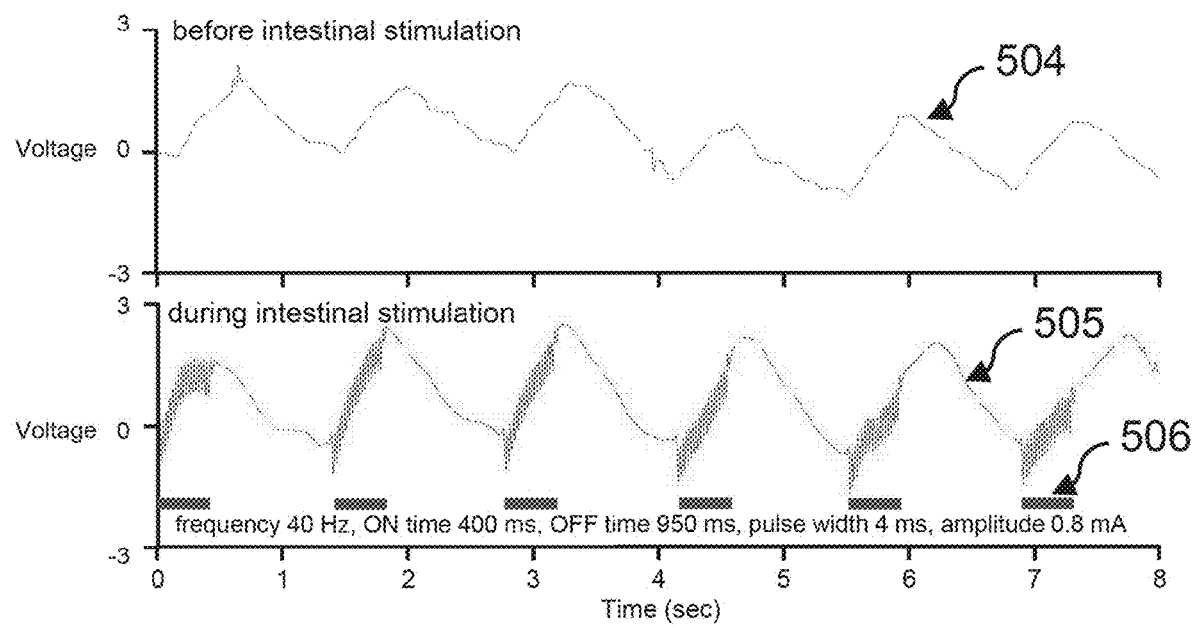
FIG. 8 graphically illustrates the delivery of electrical intestinal stimulation in synchrony with the intestinal slow wave activity.

FIG. 8 illustrates an example of the use of intestinal myoelectrical activity data collected with an intestinal myoelectrical electrode for adjusting the stimulation parameters (e.g. the stimulation frequency), in a rodent. The delivery of electrical intestinal stimulation was performed in synchrony with the ISW activity. Initially, the myoelectrical activity was collected without applying the electrical intestinal stimulation (504), and the ISW activity parameters (e.g. ISW frequency and ISW power) were extracted from the data. Then, the electrical intestinal stimulation was applied with the duty cycle and frequency matching that of the ISW frequency in the myoelectrical activity (505). The red lines indicate the times when the stimulation was applied (506). In the presented rodent preparation, the following stimulation parameters were used: frequency 40 Hz, ON time 400 ms, OFF time 950 ms, pulse width 4 ms, and amplitude 0.8 mA. As can be seen in FIG. 8, the application of electrical stimulation has enhanced the amplitude of slow wave contractions to facilitate an intestinal motility in order to improve intestinal food transit time.

Figure 9:
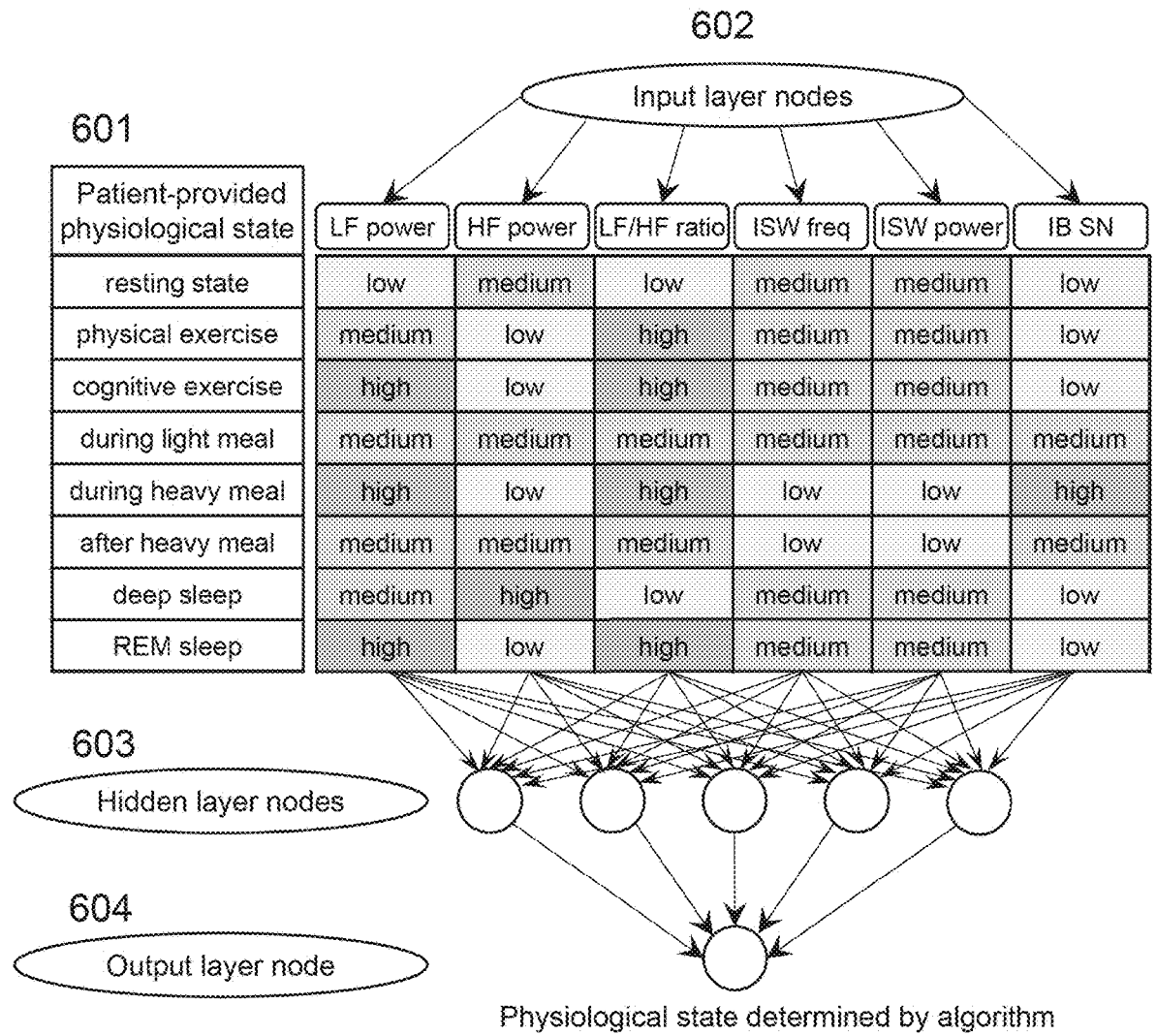
FIG. 9 is a block diagram depicting the learning phase of the algorithm during the screening phase.

FIG. 9 illustrates the learning phase of the algorithm, in which the ANN is being trained during the screening phase. The experiment was performed in a non-diseased subject, fitted with wrist-worn electrocardiographic sensor for calculating the autonomic HRV parameters (e.g. LF power, HF power, LF/HF ratio) and with a trans-nasal temporary gastrointestinal catheter with the myoelectrical electrodes located in the small intestine for calculating the ISW activity parameters (e.g. ISW frequency and ISW power), and the IB activity parameters (e.g. IB spike number (SN)). The subject provided information about various physiological states (601), such as resting state, physical exercise, cognitive exercise, during light meal, during heavy meal, after heavy meal. The physiological states for deep sleep and REM sleep were determined automatically using the data from a wrist-worn electrocardiographic sensor.

As shown there, the ANN may be structured in three layers (input, hidden, output). During the learning phase, the ANN may correlate various patient-provided physiological states (601) with various physiological parameters, which may serve as the input layer nodes (602). Correlation weights of the hidden layer nodes (603) may be assigned by correlating the input layer nodes (physiological parameters) with the output layer node (604) containing the physiological state determined by the ANN. Then, the output error between the weights for the ANN-determined physiological state (604) and for the patient-provided physiological state (601) may be calculated. For better visualization, the values for the input layer notes are represented as low, medium, and high and the nodes are shaded accordingly (low—light shade, medium—medium shade, high—dark shade).

As can be seen in FIG. 9, in some instances, the values for autonomic HRV parameters (e.g., LF power, HF power, LF/HF ratio) may be the same or similar during two or more physiological states such that it may be difficult to accurately determine the physiological state based on the autonomic HRV parameters without more. For example, the LF power, HF power, and LF/HF ratio may be high, low, and high respectively, during several physiological states, e.g., "mental exercise", "during heavy meal", and "REM sleep." Similarly, in some instances, the values for one or more of the intestinal activity parameters (e.g., ISW frequency, ISW power, IB SN, averaged intestinal temperature) may also be the same or similar during two or more physiological states. For example, the ISW frequency, the ISW power, and the IB SN may be medium, medium, and low respectively, during several physiological states, e.g., "resting state", "physical exercise", "mental exercise", "deep sleep", and "REM sleep". Thus, in some instances, it may also be difficult to accurately determine the physiological state of a patient based on the intestinal activity parameters without more. While in some physiological states, for example, "during heavy meal", the IB SN may assist in accurately discriminating between physiological states, the IB activity alone may at times be highly variable. Thus, utilization of both autonomic nervous system parameters (e.g., LF power, HF power, LF/HF ratio) and intestinal activity parameters (e.g., ISW frequency, ISW power, IB SN, intestinal temperature) may provide a more accurate determination of a physiological state of a patient. By more accurately determining the physiological states (especially for distinguishing the physiological states related to, versus unrelated to, food consumption) and adjusting the stimulation parameters accordingly, to the devices, systems, and methods described here may better control a patient's disease and/or symptoms of the disease, and may reduce the frequency and severity of unwanted side effects.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element proceeded by an "a" or an "an" does not, without further constraints, preclude the existence of additional elements of the identical type.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A method for delivering a stimulation signal to an intestinal muscle of a patient comprising:
  receiving electrocardiographic of a heart from a cardiac sensor;
  receiving myoelectrical intestinal activity data from an intestinal sensor, wherein the myoelectrical intestinal activity data is data from a duodenum, a jejunum, or an ileum of the patient;
  determining a physiological state of the patient based on the electrocardiographic data;
  calculating an intestinal activity parameter from the myoelectrical intestinal activity data;
  adjusting a stimulation signal based on the determined physiological state and the intestinal activity parameter, wherein one or more of an amplitude, a frequency, a pulse width, a burst interval, a duty cycle, and a stimulation duration of the stimulation signal is adjusted based on the intestinal activity parameter; and
  applying the adjusted stimulation signal to the intestinal muscle of the patient.

2. The method of claim 1 further comprising calculating a heart rate parameter from the electrocardiographic data.

3. The method of claim 2, wherein the heart rate parameter comprises a time-domain heart rate parameter or a frequency-domain heart rate parameter.

4. The method of claim 3, wherein the heart rate parameter comprises average heart rate.

5. The method of claim 3, wherein the heart rate parameter comprises power of a low frequency band, power of a high frequency band, or a low frequency to high frequency power ratio.

6. The method of claim 3, wherein the heart rate parameter comprises a time-domain heart rate parameter and a frequency-domain heart rate parameter.

7. The method of claim 1, wherein the intestinal activity parameter comprises an intestinal slow wave activity parameter or an intestinal bursting activity parameter.

8. The method of claim 7, wherein the intestinal slow wave activity parameter comprises an intestinal slow wave frequency or intestinal slow wave power.

9. The method of claim 7, wherein the intestinal bursting activity parameter comprises intestinal bursting duration, intestinal bursting spike number, or intestinal bursting spike frequency.

10. The method of claim 7, wherein the intestinal activity parameter comprises intestinal slow wave activity parameter and an intestinal bursting activity parameter.

11. The method of claim 1, wherein the frequency of the stimulation signal is adjusted based on the intestinal activity parameter.

12. The method of claim 1, wherein the pulse width and the duty cycle of the stimulation signal are adjusted and the adjusted stimulation signal comprises pulse width between about 1 milliseconds and about 10 milliseconds and a duty cycle between about 0.1% and about 10%.

13. The method of claim 1, wherein the intestinal muscle is intestinal muscle of a duodenum, a jejunum, or an ileum.

14. The method of claim 1 further comprising receiving intestinal temperature data from an intestinal thermal probe, wherein the intestinal activity parameter is calculated from the myoelectrical intestinal activity data and the intestinal temperature data.

15. The method of claim 1, wherein the adjusted stimulation signal is applied to the intestinal muscle of the patient using a signal delivery device and the method further comprises surgically implanting the signal delivery device or non-surgically positioning the signal delivery device.

16. The method of claim 15 wherein the method comprises non-surgically positioning the signal delivery device using a trans-nasal or a trans-oral catheter.

17. The method of claim 1, wherein the intestinal sensor is placed in a duodenum, a jejunum, or an ileum of the patient.

18. A method for delivering a stimulation signal to an intestinal muscle of a patient comprising:
receiving electrocardiographic data of a heart from a cardiac sensor;
receiving intestinal activity data from an intestinal sensor, wherein the intestinal activity data is data from a duodenum, a jejunum, or an ileum of the patient;
determining a physiological state of the patient based on the electrocardiographic data;
calculating an intestinal activity parameter from the intestinal activity data;
adjusting stimulation signal based on the determined physiological state and the intestinal activity parameter, wherein one or more of an amplitude, a frequency, a pulse width, a burst interval, a duty cycle, and a stimulation duration of the stimulation signal is adjusted based on the intestinal activity parameter; and
applying the adjusted stimulation signal to the intestinal muscle of the patient.

19. The method of claim 18, wherein the intestinal muscle is intestinal muscle of a duodenum, a jejunum, or an ileum.

20. The method of claim 18, wherein the intestinal sensor is placed in a duodenum, a jejunum, or an ileum of the patient.

21. A system for delivering an electrical stimulus to a muscle of a small intestine of a patient comprising:
a cardiac sensor;
an intestinal sensor;
an implantable signal delivery device configured to deliver a stimulation signal to the muscle;
an implantable pulse generator comprising a microcontroller configured to:
receive cardiac data from the cardiac sensor and calculate a heart rate parameter from the cardiac data;
receive intestinal activity data from the intestinal sensor and calculate an intestinal activity parameter from the intestinal activity data;
determine a physiological state of the patient based on the heart rate parameter;
adjust a stimulation signal based on the determined physiological state and the intestinal activity parameter, wherein one or more of an amplitude, a frequency, a pulse width, a burst interval, a duty cycle, and a stimulation duration of the stimulation signal is adjusted based on the intestinal activity parameter; and
instruct the implantable signal delivery device to deliver the adjusted stimulation signal.

22. The system of claim 21, wherein the muscle of the small intestine is intestinal muscle of a duodenum, a jejunum, or an ileum.

23. The system of claim 21, wherein the intestinal activity data is data from a duodenum, a jejunum, or an ileum of the patient.

24. The system of claim 21, wherein the intestinal sensor is placed in a duodenum, a jejunum, or an ileum of the patient.

25. An implantable pulse generator comprising:
a non-transitory computer readable memory comprising instructions to:
calculate a heart rate parameter from cardiac data received from a cardiac sensor;
calculate an intestinal activity parameter from intestinal activity data received from an intestinal sensor;
determine a physiological state of a patient based on the heart rate parameter; and
adjust a stimulation signal based on the determined physiological state and the intestinal activity parameter, wherein one or more of an amplitude, a frequency, a pulse width, a burst interval, a duty cycle, and a stimulation duration of the stimulation signal is adjusted based on the intestinal activity parameter; and
a microcontroller configured to execute the instructions.

26. The implantable pulse generator of claim 25, wherein the intestinal activity data is data from a duodenum, a jejunum, or an ileum of the patient.

27. The implantable pulse generator of claim 25, wherein the intestinal sensor is placed in a duodenum, a jejunum, or an ileum of the patient.

* * * * *